United States Patent
Lauks et al.

(10) Patent No.: US 7,201,833 B2
(45) Date of Patent: Apr. 10, 2007

(54) INTEGRATED SOLID-PHASE HYDROPHILIC MATRIX CIRCUITS AND MICRO-ARRAYS

(75) Inventors: Imants Lauks, Ottawa (CA); Raymond J. Pierce, Ottawa (CA); James Wojtyk, Ottawa (CA); Benoit R. Bergevin, Vankleek Hill (CA)

(73) Assignee: Epocal Inc., Ottawa, Ontario (CA)

( * ) Notice: Subject to any disclaimer, the term of this patent is extended or adjusted under 35 U.S.C. 154(b) by 541 days.

(21) Appl. No.: 10/307,468

(22) Filed: Dec. 2, 2002

(65) Prior Publication Data

US 2003/0127333 A1   Jul. 10, 2003

Related U.S. Application Data

(63) Continuation-in-part of application No. 09/871,821, filed on Jun. 4, 2001.

(51) Int. Cl.
*G01N 33/487* (2006.01)
(52) U.S. Cl. .......................... 204/600; 204/450
(58) Field of Classification Search ........ 204/450–470, 204/600–650; 436/516
See application file for complete search history.

(56) References Cited

U.S. PATENT DOCUMENTS

| | | | |
|---|---|---|---|
| 4,048,377 A | 9/1977 | Boschetti et al. | |
| 4,668,359 A | 5/1987 | Postle et al. | |
| 4,933,048 A | 6/1990 | Lauks | |
| 4,999,340 A | 3/1991 | Hoffman et al. | |
| 5,126,022 A | 6/1992 | Soane et al. | |
| 5,200,051 A | 4/1993 | Cozzette et al. | |
| 5,300,779 A | 4/1994 | Hillman et al. | |
| 5,397,451 A * | 3/1995 | Senda et al. ............. | 204/403.1 |
| 5,628,890 A * | 5/1997 | Carter et al. ........... | 204/403.05 |
| 6,004,442 A | 12/1999 | Choulga et al. | |
| 6,093,296 A | 7/2000 | Soane et al. | |
| 6,103,199 A | 8/2000 | Bjornson et al. | |
| 6,129,828 A | 10/2000 | Sheldon et al. | |
| 6,451,191 B1 * | 9/2002 | Bentsen et al. ............. | 204/600 |
| 6,488,828 B1 * | 12/2002 | Bhullar et al. ......... | 204/403.01 |
| 2002/0177238 A1 | 11/2002 | Karp et al. | |

FOREIGN PATENT DOCUMENTS

| | | |
|---|---|---|
| EP | 1 063 204 | 12/2000 |
| EP | 1063204 | 12/2000 |
| EP | 1174716 | 1/2002 |
| EP | 1 063 204 A3 | 8/2002 |
| GB | 2216258 | 10/1989 |
| WO | WO 00/043766 | 7/2000 |
| WO | WO 200136958 A1 * | 5/2001 |

* cited by examiner

*Primary Examiner*—Kaj K. Olsen
(74) *Attorney, Agent, or Firm*—Borden Ladner Gervais LLP

(57) ABSTRACT

The invention is directed to analytical devices and micro-arrays with integral fluidic inputs and outputs. The devices are constructed from planar solid-phase hydrophilic matrix circuits containing dry chemical reagents overlaying integral electro-kinetic pumping electrodes. The hydrophilic matrix circuits are enclosed within a gas permeable electrical insulator. The devices are for use in micro-scale bio-analysis, mixture separation and reaction.

55 Claims, 14 Drawing Sheets

INTEGRATED SOLID-PHASE HYDROPHILIC MATRIX CIRCUITS AND MICRO-ARRAYS

RELATED APPLICATIONS

This application is a Continuation In Part of U.S. patent application Ser. No. 09/871,821, filed Jun. 4, 2001, and entitled Integrated Electrokinetic Devices and Methods of Manufacture published as U.S. 2002/0179448 A1 the disclosure of which is incorporated herein by reference.

FIELD OF THE INVENTION

The invention is directed to analytical devices and micro-arrays with integral fluidic i/o constructed from planar solid-phase hydrophilic matrix circuits containing dry chemical reagents enclosed within a gas permeable electrical insulator for use in micro-scale analysis, mixture separation and reaction.

BACKGROUND OF THE INVENTION

Laboratory science has undergone major advances in the last decade with increases in the speed and throughput of experiments and complexity of content (number of determinations per experiment). New technology has lead to dramatic increases in both the rate of performing assays and the rate of synthesis of new chemical compounds. The large volume of sequence determinations required to elucidate the human genome necessitated the development of high throughput equipment. Contemporary experimental molecular biology continues to drive the development of equipment for both high throughput and high content performance.

The need for high throughput equipment is driven by the requirements of the pharmaceutical industry. The drivers for this are the explosions in the rate of identification of drug targets brought about by genomics and proteomics research and the rate of synthesis of new chemical compounds through combinatorial chemistry approaches. The ability to test large numbers of candidate drug compounds contained in compound libraries against large numbers of drug targets has been a bottleneck for the pharmaceutical industry.

High content equipment performs many different determinations in a single experiment. For example DNA micro-arrays and protein chips have been developed to study an ensemble of genes or proteins in a cell in a single experiment as they are affected by a particular disease or treatment.

Whether it be for nucleic acid sequence determinations, single nucleotide polymorphism determinations or gene expression experiments in the field of genomics, for protein expression or protein function studies in the field of proteomics, or for testing of compounds in drug discovery, there continues to be a need for ever higher throughput and higher content analytical equipment.

It has become apparent to molecular biologists and drug development scientists that the increase in the rate of throughput of experiments to test potential pharmaceutical compounds has not yet resulted in a commensurate improvement in the rate of drug discovery. As scientists continue to uncover the complexity of cellular processes: the vastly larger complement of proteins in the proteome than the number only recently inferred from a one protein one gene model, the subtlety of interactions between proteins in signal transduction processes, and in the orchestration of gene control by the myriad of proteins controlling transcription, they have discovered that regulatory processes (and the disease states resulting from defects in these processes) depend on pathways that are the integration of multiple signals and stimuli. Cellular processes utilize concentration dependent signaling reactions, and interactions that are both time dependent and location specific within the cell. Of the modest numbers of compounds (relative to the almost limitless quantity of $10^{60}$ potential candidate compounds) being tested in current high throughput experimentation, those showing activity towards a particular target protein or nucleic acid reaction (enhancing or inhibiting a receptor/ligand binding interaction or enhancing or inhibiting an enzyme-substrate reaction for example) typically also affect many other reactions. The subtleties and vast complexities of biological processes reveal the limitations of simplistic single factor, equilibrium or steady-state in-vitro assays that have been used in the prior-art high throughput experimentation. To more closely imitate the complex in-vivo reactions, more complex multi-parameter in-vitro assay formats are being used, including high content assays utilizing living cells within the in-vitro assay reactors. Future strategies for scale-up of experimentation will necessitate both an increase in scale and an increase in the content of experimentation to levels that were heretofore not recognized, performed in devices that do not significantly sacrifice assay performance as they are scaled to high throughput and high content. Since the pharmaceutical industry's budgets allocated to these endeavors will not increase commensurately, it is clear that technologies are needed that will perform at an order of magnitude higher throughput and content than available with technology of the current art, and at an order of magnitude lower cost per data point without sacrificing the quality of the data relative to that obtained in low throughput assays.

The most widely adopted strategy to achieve high throughput or high content in analytical equipment is to perform a large number of assays in parallel. While there have been several quite different technologic approaches to scale-up of experiments through parallel processing as discussed below, almost all have two essential features in common. First, the apparatus of the parallel process approach comprises an array of micro-reactors generally arranged on a planar solid support. Second, the route to scale-up to high throughput is through miniaturization. Target molecules, such as fragments of DNA, RNA and proteins, either in solution or in living cells or drug candidate chemical compounds are often only available in minute quantities and they are expensive. The cost of reagents and samples is the dominant cost of an experiment in today's technology. Thus, with miniaturization as the route to scale-up the quantity of reagents and sample per assay and hence the cost per assay can also be significantly reduced.

One technologic approach to high throughput parallel experimentation on arrays has been to scale-up long-established small-scale parallel experiments such as those performed on micro-plates. Planar arrays of micro-reactors in wells on micro-plates are being scaled up to high throughput by increasing the number of wells on the plate, thereby also decreasing the volume of each well (for recent examples see U.S Pat. No. 6,229,603 B1). High throughput equipment of the current art routinely employs standard sized 12.8 cm×8.6 cm plates with 96 and 384 wells. Plates with 1536 wells are now being introduced and ultra high throughput apparatus consisting of up to 9600 wells on a single standard size plate are also known. The industry would like to move to 9600 wells per plate or more. Reaction volumes in today's micro-plate technology are 1 microliter or more, but there is a need to develop devices requiring much smaller reaction volumes particularly for those applications where very little sample is available, or the reagents are very expensive.

Each well of the micro-plate array supports a discrete micro reaction. In the current art micro-liter quantities of sample are introduced into each well, along with other reagents undergoing the chemical reaction. A detector for monitoring the chemical reaction probes each well. Optical detection such as fluorimetry is a preferred approach. In a typical use of this high throughput device, aliquots of different chemical compounds are transferred from a compound library plate into the assay plate by a parallel fluid-dispensing manifold. The transfer of sample and other assay reagents is by robot-controlled fluid handling means including an array of micro-pipettors, capillary tubes, pumps and the like. Both homogeneous and heterogeneous reactions are performed in planar arrays of wells. Homogeneous enzyme-substrate reactions, and the effect of candidate drug compounds on them, can be monitored by change of fluorescence intensity using a fluorogenic substrate. Homogeneous, solution phase receptor/ligand binding reactions, and the effect of candidate drug compounds on them, can be monitored by one of a number of fluorescence based techniques the most popular being fluorescence polarization (for example U.S. Pat. Nos. 5,641,633 and 5,756,292 for fluorescence polarization assays for nucleic acids). In heterogeneous reactions a heterogeneous binding reaction takes place when one of the reactants is attached to a solid surface. Reagents or sample can be immobilized on the wells' surfaces or they can be immobilized on the surface of beads introduced into the reaction wells (for example, U.S. Pat. No. 6,210,891 B1 describing a nucleic acid primer extension reaction on a bead immobilized DNA sample).

At low levels of integration, the micro-plate reactor-array can accomplish complex experimental formats such as those with numerous reagent additions, timed reactions, washes, bead separations and the like. But these complex reaction formats are difficult and expensive to miniaturize and automate to highly parallel operation, because the fluidic input and output devices supplying chemicals to or removing chemicals from the micro-reactor wells (the fluidic i/o) become too complex. Consequently, significant resources are being applied to the extension of the use of simple and rapid equilibrium bimolecular homogeneous reaction formats that can be more easily automated to highly parallel operation and low reaction volume. Because of the time delay in delivering reagents to high density array plates, time-transient measurements are not possible. Multiple dosing of each well also has not been possible at high density. Instead dose response curves are generated from multiple wells operating the same reaction at different concentration levels of a reactant.

Workers in the field of micro-arrays have taken a different approach to parallel experiments. Micro-arrays are devices consisting of dry reagents immobilized in arrays on non-porous planar substrates. Micro-arrays perform high content assays: many heterogeneous receptor/ligand binding micro-reactions in parallel on a single sample. In these devices, the planar support surface, often a glass slide, a glass plate or a silicon wafer, consists of an array of reaction micro-locations, each location containing a different chemical compound attached to the surface of the planar substrate. In the most common form of this technology, a fluorescence reader or scanner detects the chemical reaction taking place in each micro-location. In use, the array is immersed in a bath containing sample for analysis as well as other chemicals for reaction at the planar micro-locations. Only heterogeneous reactions are performed in devices of this type. Workers in the genomics field have developed micro-arrayed nucleic acids (cDNA and oligonucleotides) attached to planar surface in which case the devices are also called gene-chips or printed DNA arrays. A series of recent review articles on this topic can be found in Nature Genetics Supplement, vol. 21(1), January 1999. Each micro-location contains a nucleic acid with a specific sequence of bases attached to the surface. Typically the base sequence of each micro-location is different. In use, the nucleic acid micro-array is exposed to a test fluid containing polynucleic acids (DNA, RNA or pDNA) to be assayed. Polynucleic acids in the test fluid have been previously labeled by attachment of a reporter molecule such as a fluorescent tag. There is a strong binding reaction between polynucleic acids in the test fluid having a base sequence complimentary to the base sequence of the nucleic acid attached to the micro-location of the array. After the binding step, a washing step removes unbound polynucleic acids from the micro-locations. The fluorescence scanner then reads the micro-array. A binding reaction at a micro-location is detected by fluorescence at that site. Nucleic acid hybridization micro-arrays have been used to perform sequencing experiments (U.S. Pat. Nos. 5,202,231 and 5,695,940) and to determine the presence of specific nucleic acid sequence variants such as single nucleotide polymorphisms (U.S. Pat. No. 5,837,832). The widest use of micro-arrays however has been in the field of gene expression (see for example chapter 7 of the book "Microarray Biochip Technology" ed. Mark Schena, Eaton Publishing 2000).

There are several variations of the nucleic acid micro-array including arrays of oligonucleotides attached to a surface (U.S Pat. Nos. 5,445,934 5,744,305 and 5,700,637), either fabricated in-situ using photolithographic masking processes (U.S. Pat. Nos. 5,405,783 and 5,489,678) and ink-jet printing (see for example T. R. Hughes et al. Nature Biotechnology. vol. 19, p342–347, 2001) or fabricated off-chip then applied to the planar substrate by an array spotter (see for example U.S. Pat. No. 5,807,522). Another variant is the cDNA array also fabricated by spotting. Genomics researchers have proposed extending the scope of the micro-array beyond nucleic acid hybridizations to include for example PCR on micro-arrays (U.S. Pat. No. 6,248,521) and primer extensions on micro-arrays (U.S. Pat. Nos. 5,547,839 and 6,210,891).

One aspect of the micro-array that has been responsible for its success is the ability to perform high content (many different receptor/ligand binding experiments: nucleic acid hybridization or protein binding) in a single batch process using very little sample and reagent. In nucleic acid hybridization for example, using a micro-array with 20,000 reaction sites on a glass slide immersed in about 1 mililiter of sample, the reaction volume of each hybridization taking place over a 100 micrometer diameter spot containing picomole quantities of attached oligonucleotide is of the order of about 50 nano-liters. Another aspect of the success of the micro-array is the inherent simplicity of the procedure. It is well known, however, that nucleic acid hybridization thermodynamics and kinetics are sequence dependent, so that for a single experimental condition the amount of hybridization occurring at two sites for which there is a positive sequence match might be quite different. For this and other reasons, the simple hybridization micro-array of the current art is not a quantitative device. Differential or comparison hybridization methods have been developed in light of this limitation (see for example chapter 7 of the book "Microarray Biochip Technology" ed. Mark Schena, Eaton Publishing 2000). In a typical differential gene expression experiment, two samples of cDNA are co-hybridized onto an array. cDNA prepared from RNA extracted from cells under study is labeled with fluorescent dye cyanine-3 (or cyanine-5). cDNA prepared from RNA extracted from control cells is labeled with cyanine-5 (or cyanine-3). The relative amount of hybridization, as measured at the two different wavelengths of the cyanine-3 and cyanine-5 fluorescence, indicates the level of expression of a particular gene in the study cells relative to the control. An approach used to control hybridization and presumably result in better quantitation is described in U.S. Pat. Nos. 5,632,957, 5,653,939 and 6,017,696 where micro-arrays with site-specific electronic addressing are taught, claiming site specific control of hybridization stringency conditions via the voltage applied to an electrode immediately under the hybridization site. Another problem with current DNA micro-array technology is the difficulty of measuring low concentrations. In the gene expression experiment, mRNAs with low abundance (one transcript per cell or less) cannot easily be determined particularly when using RNA collected from only a small number of cells. However, low concentration signaling proteins translated from low abundance mRNAs are often the most interesting to study. An enzyme amplification technique using tyramide signal amplification has been adapted to gene expression arrays to improve the detection limit by 10 to 50 fold (see for example Adler et al. in chapter 10 of Microarray Biochip Technology ed. Mark Schena).

Protein arrays using the same design principles as nucleic acid arrays have been disclosed for clinical diagnostic applications (U.S. Pat. No. 5,432,099). More recently protein micro-arrays have been developed to study protein-protein interactions in high throughput molecular biology applications (MacBeath et al. Science, 289 (5485), pp 1760–1763, 2000).

Unlike nucleic acids in the DNA micro-array experiments, which are assayed as free molecules and do not complex, proteins in a sample of cellular extract are not present just as single discrete molecules but rather they are bound in often numerous multi-molecular protein complexes. In the case of cellular protein binding, the kinetics and thermodynamics of binding reactions are particular to a protein and its binding partner. Binding constants (K) vary widely ($10^6 < K < 10^{13}$ L/mole). Binding constants of proteins to capture molecules on an array surface also will be widely varying. Binding constants of cellular proteins either one to another in complex formation or to capture molecules in an array (both free and complexed proteins being captured), are dependent on the reaction environment: temperature, pH, ionic strength, hydrophilic versus lipophilic environment, concentration of specific ions and dissolved oxygen, cofactors and the like. Also, the relative amounts of free and complexed protein will depend on the concentration and therefore will be strongly affected by the amount of dilution of the cellular extract used in an experiment.

As in a nucleic acid array, in a protein chip there are many different types of capture molecules arrayed on a planar substrate which is immersed in a sample of cellular extract. At a particular capture location, a capture molecule has been designed to capture a single particular protein molecule type (call it A) with good specificity over other proteins in the sample (one part in $10^6$ is often cited as a benchmark for specificity). The protein molecule A will be captured at that site along with multi-molecular complexes containing A (which contain other proteins including a protein B). Thus there will be many non-A proteins captured at the A capture site including protein B. At the capture site designed to specifically capture protein B there will be free B and B complexes including some protein A. Accordingly the specificity of a single capture site to its binding partner is lost. Such a device will be rendered useless unless the various components of the signal could be de-convoluted by ab initio knowledge of all of the binding constants involved. For a large multi-component array this is not practical.

Accordingly, the simple protein array immersed in a single batch of sample should not be expected to deliver quantitative data. Nor is the data from this in-vitro experimental format likely to be an accurate model of the in-vivo interactions.

Thus, a general limitation of the high content nucleic acid and protein micro-array of the current art is that they can only perform simple bimolecular heterogeneous binding reaction formats.

Yet another approach to parallel experimentation in planar arrays has been taken by the lab-on-a-chip developers. The micro-reactors of this technology comprise micro-channels and cavities formed by etching or laser ablation of material from the surface of a planar glass substrate (U.S. Pat. No. 5,180,480) or polymer substrate (U.S. Pat. No. 5,750,015). The planar substrate with formed channels and cavities is capped with an insulating cover assembly. The capped channels and cavities now form capillary conduits and chambers collectively known in the art as micro-fluidics. When there is an opening in the cap over a chamber, it becomes a well for sample and reagent introduction. Aqueous sample and reagents are dispensed into the wells using a fluid-handling manifold in much the same way as in the micro-plate technology. The dispensed fluids then fill the empty capillary conduits of the device. In many micro-fluidic methods of the prior art, pumping is by electro-kinetic propulsion in which case an electrode manifold is then brought into contact with the aqueous solutions in the wells to provide the power to electro-kinetically pump fluids from wells through the capillary conduits. In the micro-fluidic array, each micro-location of the array constitutes a micro-fluidic reactor consisting of channels and wells. In the current art, the level of parallel processing in the lab-chip array is low compared to micro-plate technology, but the technology is also amenable to automated high speed serial experimentation, so that high throughput can obtained by a combination of serial and parallel operations. In the current art, the sample volume of commercial lab-chips is about 0.1 micro-liters per experiment. Lab-on-a-chip developers have disclosed a number of different capabilities of their micro-fluidic devices, including high throughput screening of candidate drug compounds (U.S. Pat. No. 6,150,180), macromolecule separations (U.S. Pat. No. 4,908,112), nucleic acid separations (for example Woolley et al. Proc. Natl. Acad. Sci. USA Vol. 91, pp11348–11352, 1994), polymerase chain reactions (U.S. Pat. No. 6,235,471 B1) and Sanger sequencing by dideoxy chain termination and sizing by capillary electrophoresis (U.S. Pat. No. 5,661,028). U.S. Pat. No. 6,103,479 discloses an array of micro-locations with different cell binding sites and bound cells on a planar surface mated with a micro-fluidic planar substrate with etched cavities and channels.

Although complex fluid-handling capability has been demonstrated within the etched channel structures, the lab-chip devices of this art are still only lab glassware on a chip. Conventional lab-on-a-chip devices employing electro-kinetic pumping cannot be easily adapted to assay formats incorporating on-board reagents, and the supply of chemicals and reagents from off-chip sources remains a significant problem, as it is in the micro-plate devices that support complex reaction formats. Thus, here too the ability to scale multi-component complex reaction formats to small volume and highly parallel operation is limited by the ability to provide the fluidic i/o to the lab chip. One developer of high throughput screening instruments has adapted the lab-on-a-chip device to sample small volume fluid aliquots from a micro-plate. In this device a lab-chip acquires in a serial manner sub micro-liter quantities of samples for reaction from the wells of a micro-plate using an electro-pipettor (U.S. Pat. Nos. 5,942,443 and 6,235,471). The lab-chip and integral electro-pipettor step over the micro-plate sampling each well in turn. To achieve high throughput, samples are rapidly run in the lab-chip in a serial reaction format. However, this approach is limited because it only scales to high throughput when each assay can be run rapidly.

Yet another approach to parallel experimentation is the collection of methods known as solid-phase reaction formats. In these methods reactions are performed on planar slabs of porous or gelatinous materials. Devices of this art include nucleic acid arrays on porous substrates and gels such as those used in traditional blotting techniques, multi-lane gel slabs for parallel electrophoresis separations can be classified as solid phase reactions (see for example U.S. Pat. No. 5,993,634) and arrays spotted onto reagent impregnated planar gel slabs in continuous format high throughput screening technology (U.S. Pat. No. 5,976,813). In the continuous format approach, sample is spotted onto a planar porous slab that is laminated with one or more other planar slabs containing reaction reagents. At the time of the assay, sample and reagents intermix by diffusion between slabs. Using this approach, the continuous format devices avoid the fluidic i/o complexity of the other array technologies. However, the spot separation is relatively large (several milimeters) because individual reaction micro-locations must be sufficiently well separated to avoid mixing between reaction chemicals of adjacent micro-locations when they diffuse along the planar slab. Sample volumes are large, being in the 1 to 10 micro-liter range. Reagent volumes are much larger because the reagent containing slabs have large unused inter-spot areas.

In summary, high throughput micro-reactor arrays of the prior-art are limited in one of several ways. Micro-plate wells, even highly parallel 1536 well plates, at the current state of the art still require relatively large micro-liter volumes of sample and reagents. The cost per assay is thus still much too high. These devices are effective for performing single step bimolecular homogeneous reaction and can be further scaled to more parallel operation and somewhat lower volume, but they will not easily achieve the micro-reactor densities or nano-liter reaction volume achievable on micro-arrays. Furthermore, multi-component reaction formats such as those requiring timed delivery of one or multiple sample aliquots and/or multiple reagents, wash steps or purifications and separation steps are too complicated for scale-up in micro-plate technology. Lab-on-a-chip devices which operate on sub-micro-liter reaction volumes are similarly limited in ability to scale-up to highly parallel operation because of fluidic i/o complexity. Lab-on-a-chip devices operating in serial reaction format are not easily adaptable to heterogeneous binding assays and they are limited to assays with short reaction times. Continuous format gel-slab reactors use micro-liter sample volumes. Only micro-arrays of the current art exhibit highly parallel operation and have been miniaturized to tens of nano-liters reaction volumes. But they are limited in the scope of their utility, generally performing only single step heterogeneous binding reactions. Micro-arrays of the current art are further limited because the parallel reactions are run as a single batched experiment under identical conditions for all micro-locations of the array. Furthermore, micro-arrays of the current art are not very suitable for protein expression studies.

Thus there is a need for a technology that will provide complex reaction formats in high-density arrays with nano-liter reaction volumes. As a route to achieve this there is a need for a technology that will provide miniaturized, highly parallel reaction capability with simple, cost-effective fluidic i/o. To simply state the problem with prior-art technology: it has not been possible to introduce sub pico-mole quantities of chemicals dissolved in sub nano-liter quantities of solution to a micro-location of an array in real time.

SUMMARY OF THE INVENTION

It is now an object of the present invention to address the above described problems inherent in the prior-art technology. In particular, the invention is based on the principle of providing some or all of the sub nano-liter quantities of reaction chemicals to the vicinity of a reaction micro-location as dry reagents, incorporating water into the dry reagents at the time of the assay and then fluidically transporting some or all of the chemicals to the micro-location for performing the assay reaction in real time.

This object is now achieved in an enclosed hydrophilic matrix device for transport of an aqueous solute, including an electrically insulated substrate; a hydrophilic matrix path on the substrate for electro-kinetic transport of the solute, the matrix path having a pair of spaced apart contacting locations for respective electric contact with one of a pair of electrodes for producing an electric potential along the hydrophilic matrix path; at least one of the pair of electrodes being supported on the substrate and having a contact end for connection to an external circuit for supplying power and a matrix end for electric contact with the hydrophilic matrix; the matrix being initially dry and including a humectant for increasing a water absorption rate of the matrix; an insulator enclosing the hydrophilic matrix for sealing the matrix between the insulator and the substrate, the insulator being impermeable to the solute and water vapor permeable; an orifice being provided in the insulator above the matrix to allow an aqueous solute species to be transported into and out of the matrix through the insulator.

In a preferred embodiment, both of the pair of electrodes are supported on the substrate and each have a contact end for connection to the external circuit for supplying power and a matrix end for electric contact with the hydrophilic matrix.

In another preferred embodiment, the substrate has a pair of opposite surfaces, the matrix path is supported on one of the substrate surfaces and at least one of the pair of electrodes is supported on the other substrate surface, the substrate being shaped and constructed for providing electrical contact of the matrix with the electrode on the opposite substrate surface.

In still another preferred embodiment, the substrate includes a passage for physical and electrical contact of the matrix at one of the contacting locations with the electrode on the opposite substrate surface.

In a further preferred embodiment, the hydrophilic matrix device in accordance with the invention for the transport of an aqueous solute, includes an insulated substrate, a pair of electrodes supported on the substrate, each electrode having a contact end for connection to an external circuit for supplying power and a matrix end for electric contact with a hydrophilic matrix, a hydrophilic matrix path on the substrate for electro-kinetic transport of the solute, the matrix path having a pair of contact locations for electric contact with the respective matrix ends of the electrodes, an insulator enclosing the hydrophilic matrix for sealing the matrix between the substrate and the insulator, the insulator being substantially impermeable to the solute, and an orifice in the insulator above the matrix for the passage of an aqueous solute into or out of the matrix through the insulator.

The matrix is preferably initially in a dry and inactive state in which it is substantially non-conductive and is transferred into a humidified, conductive state by incorporation of water. Water can be incorporated by capillary action through the orifice, or a separate wet-up opening in the insulator and/or by transport through the insulator.

Humidification or wet-up of the matrix is preferably improved by inclusion of a humectant in the matrix. For the purposes of this disclosure, the term humectant refers to a neutral molecule which when dissolved in water forms an aqueous solution with a water vapor pressure significantly less than pure water at a concentration where the solution's viscosity is not significantly higher than pure water. The humectant is preferably a low molecular weight molecule. Examples of humectants applicable for use in devices in accordance with the invention include urea, alanine, orthinine, praline, lysine, glycine, polyols and sugars: sucrose, glucose, xylitol, sorbitol, mannitol, lactose, maltose, lactulose, glycerol, propylene glycol, citric acid, tartaric acid, malic acid.

Electric contact between the matrix and the electrodes at the contact locations is preferably achieved either by direct physical contact between the electrode and matrix materials at the contacting locations or, in the case where the matrix and electrodes are spaced apart at the contacting locations, by way of an intermediate conductive substance which may be permanently present or produced upon wet-up of the matrix.

In one aspect, the invention provides devices with integral fluidic i/o and integral dry chemical reagents. The devices preferably consist of a micro-location or array of micro-locations, each micro-location typically having integral fluidic i/o containing integral dry chemicals.

For the purposes of this description, the term micro location refers to a defined location on a substrate including a chemical attached to the substrate. The term micro-array includes an array of such micro-locations for the performing of high content assays, i.e. many micro reactions (one pre micro-location) in parallel.

The device preferably also includes at least one micro-reactor. Micro-reactors in accordance with this invention are sites in which chemical reactions can take place. The integral fluidic i/o is preferably constructed to pump integral chemical reagents from integral reservoirs to or from the micro-reactors. Micro-reactors with integral chemical reagents according to this invention avoid the complex fluidic i/o of prior-art technologies where, in addition to the sample, the chemical reagents required for an assay must be supplied to the prior art micro-reactors from external non-integral locations. Accordingly, devices in accordance with the invention expand the uses of parallel micro-reactor technologies to applications where the cost and complexity of prior-art devices using complex fluidic i/o devices would be prohibitive and to applications where the performance of prior-art devices with non-integral reagents is inadequate.

In one preferred embodiment, the devices of this invention allow highly parallel, high throughput experiments at densities of up to 10,000 per square centimeter of surface using as little as pico-liter to nano-liter quantities of sample and reagents (pico-moles or femto-moles of dry reactants).

In another preferred embodiment, the devices of this invention provide arrays with instrument control (including feedback control) of the integral fluidic i/o for transport of chemicals to individual reaction sites in real time and enabling site-specific reaction conditions.

The devices of this invention can perform a broad range of different experimental formats including complex formats in a highly parallel manner. These include both homogeneous and heterogeneous assays, multiple-reagent reaction formats, reaction formats requiring timed reagent introductions and data acquisition for time-transient assays, multifold single-component additions for dose response curves or titrations. The devices of this invention can perform biochemical assays on aqueous media on beads contained within aqueous media, or assays on biological cells contained within micro-locations.

In a further preferred embodiment, the invention provides micro-reactors and micro-reactor arrays connected to integral fluidic i/o comprising circuits constructed from planar solid-phase hydrophilic matrixes containing dry chemical reagents enclosed within an insulator layer. The micro-reactors with fluidic i/o implemented using enclosed hydrophilic matrixes are intended for use in micro-scale analysis, mixture separation and reaction. Devices and methods of manufacture related to those disclosed herein are disclosed in co-pending application Ser. No. 09/871,821 Integrated Electro-kinetic Devices and Methods of Manufacture" published as U.S. 2002/0179448A1.

In yet another embodiment, the invention provides micro-reactors and micro-reactor arrays with integral fluidic i/o wherein each reactor also contains at least one integral dry chemical.

In still another preferred embodiment, the invention provides devices including at least two arrays on separate substrates which, when brought into close proximity and aligned one to the other, form an array of micro-reactors.

Fluidic I/O By Enclosed Hydrophilic Matrix Circuits

The integral fluidic i/o aspect in accordance with this invention is preferably implemented using enclosed hydrophilic matrix circuits. Each enclosed hydrophilic matrix circuit preferably includes a formed hydrophilic matrix structure, manufactured as an essentially dry solid-phase entity. In one embodiment, regions of this hydrophilic matrix preferably contain dry chemicals.

For the purposes of this disclosure, the operational definition of the dry state is that in this state non-immobilized chemicals in the solid-phase hydrophilic matrix (i.e. those not chemically attached to an immobile solid support) are substantially neither transportable nor capable of reaction with each other. The dry-reagents within the dry hydrophilic matrix are thus positionally and chemically stable after manufacture and during storage.

The hydrophilic matrix is preferably enclosed by a surrounding insulating medium that is substantially non-conducting for both neutral molecules and charged species. For the purposes of this disclosure, the substantially non-conducting property of the insulating medium also has an operational definition. The insulating medium preferably confines the chemicals contained within the circuit and excludes from the circuit deleterious contaminants present in external phases. Also, the insulating medium must be sufficiently resistive to electrical current flow, so that any voltage applied to the hydrophilic matrix for the purpose of electro-kinetic transport is not short-circuited.

In one preferred embodiment, the enclosing insulating medium however is at least in part water vapor permeable so as to enable incorporation of water into the dry matrix at or before the point of use.

In another preferred embodiment, the hydrophilic matrix is micro-porous and capable of water incorporation by capillary flow from an orifice in the insulator. Incorporation of water converts the hydrophilic matrix from the operationally inactive, dry state to a hydrated, active state. In its active state the hydrophilic matrix permits transport of chemicals from location to location within the enclosed circuit and permits reactions between chemicals contained within the enclosed circuit. Species transport through the active hydrophilic matrix is by at least one active pumping means, preferably electro-kinetic.

Electro-kinetic transport includes both electrophoretic and electro-osmotic transport, in which latter case at least a part of the hydrophilic matrix itself or its enclosing walls comprise a fixed surface charge and a zeta potential. For electro-kinetic transport through an enclosed hydrophilic matrix circuit at least two integral electrodes are used which contact the enclosed hydrophilic matrix at two spaced-apart locations so as to allow power transmission for electro-kinetic transport. Each hydrophilic matrix circuit has at least one orifice through the enclosing insulating medium to permit transport of species into or out of the enclosed hydrophilic matrix circuit.

A preferred enclosed hydrophilic matrix circuit in accordance with the invention comprises circuit elements. These circuit elements include regions and paths. Regions preferably contain chemicals, paths connect regions and permit transport of chemicals between regions. A voltage difference along a path, when supplied by two integral spaced-apart electrodes, powers the electro-kinetic transport of species through the path. A typical circuit according to one embodiment includes reservoir regions in which chemicals are stored, regions where chemicals will be mixed, regions to which chemicals are pumped, regions for chemical reaction, regions where chemicals will be separated and regions where chemicals will be detected or their chemical concentrations measured. Upon incorporation of water through an at least in part water permeable surrounding insulator, the enclosed hydrophilic matrix circuit with its regions and paths becomes operationally active enabling all of the circuit's functions outlined above.

In a preferred embodiment, the micro-reactor or micro-reactor array and integral fluidic i/o supplied by enclosed hydrophilic matrix circuits are substantially planar.

In another preferred embodiment, the devices are manufactured by micro-fabrication.

In another preferred embodiment, the devices are unit-use disposable.

In another preferred embodiment, the devices are manufactured as solid-phase dry reagent devices.

In another preferred embodiment, the transport of species through the enclosed hydrophilic matrix circuit is electro-kinetic and is powered by integral electrodes.

Configurations of Micro-reactors, Integral Fluidic I/O and other Fluidics

The invention also provides various configurations of micro-reactors and fluidic i/o. In these configurations as described below, an enclosed hydrophilic matrix circuit generally provides integral fluidic i/o to one or more micro-reaction sites. That is to say, the enclosed hydrophilic matrix circuit can, i) supply chemicals to a micro-reaction site and/or ii) extract chemicals from the micro-reaction site. Chemicals can be extracted from the micro-reaction site and moved to a waste area contained within the enclosed circuit, or moved through the enclosed circuit to another location for subsequent further reaction at another micro-reaction site. Chemicals can be extracted from the micro-reaction site to a location within the circuit or to another adjoining circuit of the device for component separation and analysis.

Several configurations of micro-reactors or micro-reactor arrays and integral fluidic i/o are contemplated within the framework of the present invention. In one configuration, a micro-location or an array of micro-locations each contain at least one micro-reactor. Integral fluidic i/o provided by an enclosed hydrophilic matrix circuit supplies reagents to many micro-reactors within an array or to the array as a whole. In use, such fluidic i/o preferably supplies chemicals to reactions performed in common on the entire sample batch. Because the integral fluidic i/o of this configuration can supply or remove chemicals in volumes of 0.1 to 100's of micro-liters to and from the array as a whole, it is referred to herein as integral micro-fluidic i/o. For example, such integral micro-fluidic i/o preferably supplies integral reagents to perform pre-analytical reactions on a sample as a whole. Pre-analytical reactions can include cell lysis or amplification and labeling reactions.

In another configuration in accordance with the invention, there is a micro-location or an array of micro-locations wherein each micro-location contains at least one micro-reactor and integral fluidic i/o. In each micro-location the integral fluidic i/o is provided by an enclosed hydrophilic matrix circuit that supplies reagents to the individual associated micro-reactor within the micro-location. Because the fluidic i/o of this configuration will supply chemicals to or remove chemicals from an individual micro-reactor of the array in nano-liter or less volumes, it is referred to herein as nano-fluidic i/o. In yet another configuration of this invention there are micro-reactors or micro-reactor arrays in which both integral micro-fluidics and nano-fluidics i/o are utilized together.

This invention also contemplates micro-reactors or micro-reactor arrays in which the integral micro-fluidics and/or nano-fluidics i/o which are implemented using the enclosed hydrophilic matrix circuits according to this invention are combined with conventional fluidic elements of the known art. Thus, within the framework of this invention, micro-reactors or micro-reactor arrays with integral micro-fluidic or nano-fluidic i/o can be combined into the micro-well of a micro-plate device or into the channel of a micro-fluidic lab-chip.

Still further configurations of micro-reactors and fluidic i/o in accordance with the invention are implemented using enclosed hydrophilic matrix circuits and other modes of connection to conventional fluidic elements.

In one preferred configuration, a planar substrate is used having one or an array of micro-locations including a micro-reactor and an enclosed hydrophilic matrix circuit. The enclosed hydrophilic matrix circuit contains at least one reservoir with chemicals for transport along a path to the micro-reaction site. There is an orifice through the insulator of the enclosed hydrophilic matrix circuit connecting the circuit to the adjacent micro-reactor. The micro-reactor is a well into which sample fluid is introduced from an external source. The wells can be micro-fabricated on the same planar substrate as the enclosed hydrophilic matrix circuits, or formed as a separate planar element much like a conventional well of a planar micro-plate (except without a bottom). The well is then aligned to the substrate and assembled to mate each well with an enclosed hydrophilic matrix circuit of an array. The final device resembles a conventional micro-plate except that there are integral fluid i/o elements consisting of enclosed hydrophilic matrix circuits on the base of each well. Sample fluid is introduced into each well from a dispensing nozzle, as it is in conventional micro-plate technology, or introduced along a channel formed in the well-plate and connected to the well. Then, at least one other reactant is pumped under instrument control into each well from the enclosed hydrophilic matrix circuit on the well base while concurrently monitoring the reactions by optical scanning from the top or through the base when the planar substrate supporting the enclosed hydrophilic matrix circuits is transparent.

In another preferred configuration in accordance with the invention, a planar substrate is used with micro-locations consisting of micro-reaction sites adjacent to enclosed hydrophilic matrix fluidic i/o circuits. The enclosed hydrophilic matrix circuit contains at least one reservoir with chemicals for transport along a path to the micro-reaction site. The micro-reaction site includes a solid-phase support element onto which a sample or reagent is fluidically dispensed from an external source (from a micro-printing or dispensing device of the known art). The reaction site can consist of a porous solid-phase element into which dispensed solution is absorbed, or a non-porous surface onto which material is dispensed. In this embodiment, the micro-reactor sites with dispensed chemicals are micro-fabricated on the same substrate as the enclosed hydrophilic matrix circuits. Reactions occurring in individual micro-locations are either separated by well walls as in the previous embodiments or by hydrophobic barriers as are known in the art.

In another preferred embodiment in accordance with the invention, a first and second planar substrates are placed spaced apart parallel to one another and individual micro-locations are gasketed from one another. The first planar substrate has micro-locations including micro-reaction sites adjacent to enclosed hydrophilic matrix fluidic i/o circuits. The enclosed hydrophilic matrix circuit contains at least one reservoir with chemicals for transport along a path to the micro-reaction site. The second planar substrate consists of an array of micro-locations with the same step-and-repeat dimensions as the array on the first substrate, with dry chemicals formed at each micro-location. The arrays of dry chemicals might be candidate drug compounds for testing, in which case they dissolve in aqueous solution when the test is performed, or they can be an array of chemicals attached to the substrate that do not dissolve such as receptors, ligands, receptor-ligand complexes or receptor-ligand complexes with reporters. The first and second substrates are brought into close proximity and aligned so that the micro-locations on each substrate align opposite to one another. An aqueous solution is flowed between the two plates while in close proximity. Next, the two surfaces of the two plates are brought into contact with a gasket element which keeps the plates closely spaced apart and forms a wall around each micro-location. The aqueous fluid is thereby divided into separate portions, one for each individual micro-location. The completed device resembles a micro-plate array of filled wells with a cover plate, except that the cover plate also supports an array of micro-locations with chemicals and the base of the wells consists of an array of enclosed hydrophilic matrix circuits. It is evident from this arrangement that either plate can constitute the top or bottom plate. At least one plate is preferably transparent for optical measurement of the reactions within each micro-location. In other variants of this twin-plate configuration, arrays of micro-locations with enclosed hydrophilic matrix circuits are found on both plates. In still other possible variants, arrays of dry chemicals are provided on both plates or arrays of both enclosed hydrophilic matrix circuits and dry chemical arrays are provided on both plates. After preparation of the two plate sandwich, at least one other reactant is pumped under instrument control into each well from the at least one enclosed hydrophilic matrix circuit within each micro-location while concurrently monitoring the reactions by optical means.

In another configuration, an orifice is provided through the insulator of the enclosed hydrophilic matrix circuit for connecting it to a channel. Preferably, the channel is microfabricated on the same planar substrate as the enclosed hydrophilic matrix circuit or is a conventional micro-fluidic channel formed by etching or ablation in another planar insulating element that is then assembled to the planar enclosed hydrophilic matrix circuit. The completed device resembles a conventional lab-on-a-chip device consisting of a substrate with channels and a top cover plate except that the cover plate now also contains micro-locations with enclosed hydrophilic matrix circuits.

In those embodiments of this invention in which there is an aligned pair of planar substrates, an alignment and assembly device is preferably used which is similar to the apparatus used in conventional photolithography for aligning a planar semiconductor wafer with a planar mask plate.

Fluidic I/O Configurations Associated With Different Assay Formats

In one application of the devices in accordance with the invention, the enclosed hydrophilic matrix fluidic i/o circuit is used to fluidically pump chemicals into an adjacent micro-reactor. In such an application, the enclosed hydrophilic matrix circuit comprises a path connecting to a reservoir region of the hydrophilic matrix containing chemicals to be supplied to the micro-reactor, and the path has an effluent region fluidically connected to the micro-reactor through an orifice in the enclosing insulator of the circuit. At least one electro-kinetic pumping means is provided for transporting chemical from the enclosed reservoir region along the enclosed path to the micro-reactor. In one variant of this embodiment, the path is dimensioned to be sufficiently long so that the amount of chemicals entering the micro-reactor due to diffusion along the path is minimal during the period prior to active pumping of chemicals to the micro-reactor. In another variant, an air space is provided in the path between the reservoir and the effluent region connecting to the micro-reactor to prevent diffusional transport of chemical to the micro-reactor. Thus, material must be transported fluidically by convective flow of the fluid along the path, the fluid traversing the air gap when it is actively pumped. Integral electro-kinetic pumping electrodes are located in the enclosed hydrophilic matrix circuit upstream of the air gap. For example, one electrode is located in the reservoir region and another in the path just upstream of the air gap. In another variant, the reservoir is dimensioned with circular geometry to permit print-deposition of chemicals during the fabrication of the enclosed hydrophilic matrix circuit. In yet another variant there is a pump reservoir and a transport path with spaced apart integral electrodes to supply power to transport fluid along the path. The path is further fluidically connected to a second reagent reservoir containing chemicals to be pumped. The reagent reservoir is downstream of the pump reservoir and path and its integral electrodes. The reagent reservoir is fluidically connected to the micro-reactor through an effluent orifice in the enclosing insulator.

In another application of the devices in accordance with the invention, the enclosed hydrophilic matrix fluidic i/o circuit is used to extract chemicals from an adjacent micro-location into the circuit. In one configuration of this embodiment, a planar substrate with micro-locations consisting of micro-reactors and adjacent enclosed hydrophilic matrix fluidic i/o circuits is connected to a source of chemical through an orifice in the insulator of the enclosed hydrophilic matrix circuit to permit chemicals to enter the circuit and move along a hydrophilic matrix path to another micro-reaction site, which is also enclosed. Another example is the extraction of chemicals from a micro-reactor into an adjacent separation device contained within the enclosed hydrophilic matrix circuit. Such a device can be used, for example, in the electrophoretic separation of bound from unbound components in a ligand-binding reaction taking place in the adjacent micro-reactor. In that configuration, a planar substrate with micro-locations consisting of enclosed hydrophilic matrix circuits and adjacent micro-reactors is also supplied with chemical through an orifice in the insulator of the enclosed hydrophilic matrix circuit to permit chemicals to enter the circuit and move along a separation path which is also enclosed. When labeled reactants in the micro-reactor are thus drawn into the separation device of the enclosed hydrophilic matrix circuit they are electrophoretically separated and measured. As is known in the art of conventional electrophoresis separation, the measurement occurs by probing a particular location within the separation path of the enclosed hydrophilic matrix circuit, preferably using optical means when the labels are colorimetric, fluorescent or luminescent.

Many other possible arrangements of fluidic i/o around the micro-reactor according to the requirements of the assay formats are contemplated within the framework of the present invention. For example, in one application a micro-reactor is supplied with several reagents from several different, independently-pumped fluidic input reservoirs and fluid is pumped out of the micro-reactor to other locations including separation devices and waste chambers. An assay format can be classified according to whether it is homogeneous or heterogeneous; bimolecular or multi-molecular; steady-state, equilibrium or time transient measurement; single factor or multiple factor experimental design. In this embodiment, a micro-reactor and an adjacent enclosed hydrophilic matrix circuit are provided within each micro-location of an array of micro-locations, whereby the circuit configuration depends on the fluidic i/o requirement of the assay type being run in the micro-reactor. Specific inventive configurations of bioassays with integral fluidic i/o are recited below.

Heterogeneous Binding Assays and Combinatorial Methods

Heterogeneous receptor/ligand binding reactions of particular interest in high throughput molecular biology and high throughput testing of candidate drug compounds are those involving nucleic acids and those involving proteins.

In a preferred heterogeneous micro-reaction array using a device according to this invention, each micro-location comprises a micro-reactor with immobilized capture molecules for performing one or more receptor-ligand heterogeneous binding reactions, wherein the micro-reactor is either adjacent to or contained within an enclosed hydrophilic matrix nano-fluidic i/o circuit. The enclosed hydrophilic matrix circuit comprises at least one reservoir region containing one or more chemicals and at least one path along which chemicals can be actively pumped from the reservoir to the reactor. It is possible to pump some or all of the following assay reaction components: the ligand, a drug compound for testing, a reporter molecule or a substrate for an enzyme reporter. Specific examples are described below.

In a typical heterogeneous bimolecular receptor/ligand binding assay known in the art, one of the receptor/ligand pair, say the receptor is attached to a solid surface. The other of the pair, in this case the ligand, is in solution. When the solid surface with attached receptor (the capture site) is bathed in the solution containing ligand (the target) a binding reaction occurs between receptor and ligand forming a receptor-ligand complex now attached to the surface. A reporter molecule is attached to the ligand either before the receptor/ligand binding step, as is typical in the gene expression experiment, or during or after the receptor-ligand binding reaction, as in a one or two step sandwich immunoassay known in the art. Colorimetric, fluorescent, luminescent and electrochemical labeling molecules are all well known in the art for use in the so-called direct labeling technique. Also known in the art is the use of enzymatic reporter systems. In this case, an enzyme is attached to the ligand and the presence of the receptor/ligand complex is reported by the detection of enzymatic conversion of a substrate. Usually the product molecule is detected. Chromogenic, fluorogenic, luminogenic and electrogenic substrates that produce detectable products are well known in the art. In heterogeneous binding formats it is necessary to separate unbound reporter molecules from the vicinity of the bound reporters. The concentration of bound reporter molecules, indicating the concentration of receptor/ligand complex, is then detected by absorbance, fluorescence, luminescence or electrochemically.

Perhaps the simplest advantageous use of a device in accordance with the invention in heterogeneous assays is to provide a high density receptor-binding micro-array that is sensitive to small quantities of analyte by using enzyme amplification. In direct labeling techniques, the detected entity is chemically attached to the receptor-ligand complex, so that the detected signal from a micro-location of an array determines the concentration of complex at that micro-location. As noted earlier however, the prior-art micro-arrays that use direct labeling techniques are insensitive to small quantities of analytes, either when they are in low abundance per cell or when there is a small quantity of cells. The limit of detection can be significantly improved by labeling with an enzyme. Each enzyme molecule converts hundreds or thousands of substrate molecules per second giving hundreds or thousands of detectable molecules per second per enzyme-ligand-receptor complex. However, since the enzyme reaction occurs in solution, the product of the enzyme reaction occurring at a given micro-location must be kept in the vicinity of the enzyme-ligand-receptor-complex at that micro-location otherwise the detectant moves to a neighboring micro-location rendering the array useless because of signal cross-talk between array micro-locations. For this reason such a reaction scheme has been possible only in the lower density micro-plate format where each micro-location is a reaction well containing reaction solution separated from its neighbors by a well wall, but not in the high density micro-array format where the reaction solution is continuous (except in the case of the tyramide signal amplification scheme where the enzyme reaction product becomes attached to the solid surface in the vicinity of the reaction micro-location. But there is still loss of resolution and the amplification is only 10 to 50 fold.). To achieve the desired result on a high density micro-array one must isolate each reaction micro-location before the enzyme amplification step, then conduct the enzyme amplification by applying substrate individually to each micro-location. This can be achieved with one embodiment of a device of the present invention as follows. In this embodiment, a planar substrate has an array of micro-locations each including a micro-reactor with receptor-ligand binding sites and an adjacent enclosed hydrophilic matrix circuit with an orifice in the insulator connecting the circuit to the micro-reactor. Within the enclosed hydrophilic matrix circuit at least one reservoir region is provided which contains enzyme substrate molecules. The enzyme substrate molecules are not chemically attached to the matrix or the planar support so that they are transportable along a path within the circuit. At least one path connects the at least one reservoir region to the micro-reactor and at least one pumping means is provided for transporting enzyme substrate molecules from the at least one reservoir region to the micro-reactor.

In the use of this particular embodiment, the array of micro-locations comprising capture sites is exposed to a test solution. Receptor-ligand complexes form at each micro-location. In one variant of this experiment the target molecules in the sample solution are first labeled with an enzyme using techniques known in the art, before they are presented to the capture array for formation of receptor-ligand-enzyme complexes. In another variant, the target molecules are labeled with a biotin molecule using techniques known in the art, and the biotin labeled targets are then presented to the capture array for formation of receptor-ligand-biotin complexes. The array is then overlaid with a solution containing enzyme linked to streptavidin for the formation of receptor-ligand-biotin-streptevidin-enzyme complexes. A second plate is mated with the capture array plate so as to isolate individual micro-locations from one another, preferably by sandwiching the second plate over the capture array plate. Each micro-location now contains a micro-reactor filled with an aqueous solution, a capture surface with capture complexes and an adjacent enclosed hydrophilic matrix circuit. By now activating the pump at each individual micro-location, enzyme substrate is injected into the micro-reactor from the enclosed hydrophilic matrix circuit while the extent of enzyme reaction is concurrently detected by scanning each micro-location. There are three ways to perform the experiment. In one the capture array is on a first planar substrate and the enclosed hydrophilic matrix circuit is on a second. Capture complexes are formed on the first plate, then the two plates are aligned and contacted to form the individual reaction micro-locations for enzyme reaction. In the second way, the capture array and the enclosed hydrophilic matrix circuit array are on the same plate. Capture complexes are formed on this plate which is then mated with a second, blank cover plate to form the individually separate micro-locations for enzyme reaction. In the third way, the capture array and the enclosed hydrophilic matrix circuit array are on the same plate, one array element of each at each micro-location. Micro-locations are separated by a hydrophobic surface which divides the reaction solution into individual reaction solutions portions respectively contained over individual micro-locations. Then the enzyme substrate is pumped from the enclosed hydrophilic matrix circuit into the reaction solution at each micro-location. The device can be used to obtain both high sensitivity gene expression DNA chips as well as protein chips. It is advantageous to use the invented device in applications of gene expression or protein expression where the supply of starting material is limited. The invented device is particularly useful for high sensitivity protein chips where nucleic acid amplification schemes are not available.

Another advantageous use of the invented device is in chemiluminescent labeled ligand-receptor assay formats adapted to high density arrays. Of the methods of signal generation known in the art, chemiluminescence is the preferred method for a bioassay of low abundance chemicals. In particular, enzyme amplified ligand-receptor assays with luminogenic detection have proven the most sensitive assay method in the art. As in the above example of enzyme amplification, the chemiluminescent light generating reaction also takes place in solution. The product of the reaction occurring at a given micro-location must be kept in the vicinity of the ligand-receptor-complex at that micro-location, otherwise the light generating detectant moves to neighboring micro-location rendering the array useless because of signal cross-talk between array micro-locations. For this reason such a detection scheme has been possible in the lower density micro-plate format where each micro-location is a reaction well containing reaction solution separated from its neighbors by a well wall, but it has not been achieved in the high density micro-array format where the reaction solution is continuous. This problem is now addressed in one embodiment of the device of the invention directed to chemiluminescent assays wherein an array of micro-locations each including a micro-reactor with receptor-ligand binding sites is connected through an orifice in the insulator to an adjacent enclosed hydrophilic matrix circuit. At least one reservoir region within each enclosed hydrophilic matrix circuit contains one or more chemiluminescence assay reagents. These reagents are not chemically attached to the matrix or the planar support so that they are transportable along a path within the circuit. There is at least one path connecting the at least one reservoir region to the micro-reactor and at least one pumping means for transporting chemiluminescence assay reagents from the at least one reservoir region to the micro-reactor. The reagents may be one or more of the following: luminogenic enzyme substrate (if the assay is enzyme amplified) or a chemiluminescent precursor, a chemiluminescence initiator or a catalyst as are commonly used in the art of chemiluminescence assays. The ability to add the chemiluminescent assay reagents in-situ by pumping them from the reservoir region permits flash type chemiluminescent assays which are not easily implemented in devices with non-integral fluidic i/o devices.

It also permits low level detection, because the background light level (immediately before addition of reagent from integral fluidic devices) can be subtracted from the signal light level immediately after addition of the reagents.

Another advantageous application of the device in accordance with the invention is to investigate multi-molecular complexes. In this application, the heterogeneous binding reaction forms a three-molecule sandwich between immobilized capture molecules, target molecules from the sample being assayed and reporter molecules. The device of this embodiment includes an array of micro-locations with receptor-ligand micro-reaction sites. Each micro-reaction site is brought into contact with an aqueous solution containing the target molecules to be assayed. Target molecules in the aqueous solution bind to respective capture molecules attached to each micro-reactor in the array. An integral electro-kinetic pump within an enclosed hydrophilic matrix circuit is provided at each micro-location, which pump is activated under external instrument control. The pump delivers reporter molecules to the micro-reactor. Reporter molecules bind to attached target molecules, if present. A wash step removes unbound reporter molecules. A detection step consisting of measuring the presence of label at each micro-reactor location completes the assay.

Several formats of heterogeneous binding assays with three-molecule sandwich complexes using devices of this invention are contemplated. In one preferred format, each micro-reaction site at each micro-location contains identical capture sites and each reporter reservoir region within the hydrophilic matrix circuit contains different reporter molecules. Each of the identical micro-reactors of the array contains one or more attached capture molecules that capture target molecules with specific composition. In an alternative application, the array of identical micro-reaction sites comprises non-specific capture sites. For an array containing M rows and N columns there are MN elements containing MN different compositions of reporter molecules and 1 capture site composition (specific or non-specific). Thus there are MN different 3 molecule sandwiches of capture molecule, target molecule and reporter molecule.

In another preferred format, the reporter reservoir region can be doubly printed so that there are M reporters printed by row in the first pass, then N by column in the second pass. There are thus MN two reporter combinations for M+N different original individual chemical compositions obtained by this combinatorial print format. In one variant of this format, all reporters are labeled with the same fluorescent tag. In another variant only one of the two reporters is labeled. In another format, each reporter reservoir region contains more than one reporter each having a different label with its own unique fluorescence wavelength.

In yet another preferred format of the above three-molecule sandwich type array, each micro-reaction site at each micro-location contains different capture molecules and each reservoir region contains the same reporter molecules. For an array containing M rows and N columns there are MN elements containing MN different compositions of capture molecules and 1 reporter molecule. Thus there are MN different 3 molecule sandwiches of capture molecule, target molecule and reporter molecule.

In yet a further preferred format, each micro-reaction site at a different micro-location contains different capture molecules and the reservoir regions contain different reporter molecules. For example, an array containing M rows and N columns can have M different capture molecule compositions, the same composition on each row element, and N different reporter molecule compositions, the same composition on each column element. MN elements containing M different capture molecules and N different reporter molecules. Thus, there are MN different 3 molecule sandwiches of capture molecule, target molecule and reporter probe molecule. But there are only M+N compositionally different capture or reporter molecules combined. In this combinatorial format MN different target molecules can be discriminated by only M+N reagents. For example, a chip with 1000 different capture molecules and 1000 different reporters can distinguish 1,000,000 different target molecule compositions.

It is also anticipated within the framework of this invention, that many other location specific combinatorial formats are possible with the invented device, including ones where target molecules also are labeled and ones where multi-wavelength label systems are incorporated providing additional multiplexing capability.

In another example of a heterogeneous reaction using the micro-reactor array with integral nano-fluidic i/o, an array of protein binding reactors or a nucleic acid hybridization reactors with integral labeling and enzyme amplification reagents is used.

Homogeneous Assays

A representative example of a homogeneous reaction performed on a device of this invention is an enzyme assay for drug testing. Candidate drug compounds are of potential interest if they cause a change in the reaction rate of a particular enzymatic reaction. Such an assay can be formatted to give an optically detectable reaction rate by use of chromogenic, fluorogenic or luminogenic subtrate: a synthetic substrate for the enzyme which becomes fluorescent or luminescent upon enzymatic reaction. This and numerous other schemes are known in the art for formatting an enzyme reaction whose rate is measured by optical means. The specific construction and setup of the micro-locations and hydrophilic matrix circuits of the device of the invention required for carrying out this homogenous assay is apparent from the above discussion of different embodiments of the device of the invention.

Complex Reaction Formats

A representative example of a complex reaction format which can be performed on an array according to this invention is a pyrosequencing reaction format. In this method the four nucleotide bases are added in sequence to a reactor containing a growing DNA chain on a DNA template. There is release of inorganic pyrophosphate upon incorporation of a base as known in the art (U.S. Pat. No. 6,210,891). This technique uses the enzymatic luminometric inorganic pyrophosphate (PPi) detection assay (Nyren and Lundin, Anal. Chem. 151, 504–509, 1985) which is known in the art and based on the following reaction sequence $$PPi + APS \xrightarrow{\text{ATP-sulfurylase}} ATP + SO_4^{2-}$$

$$ATP + \text{luciferin} + O_2 \xrightarrow{\text{luciferase}} AMP + PPi + \text{oxyluciferin} + CO_2 + \text{light}$$

The complex assay of the above example that requires a reactor to which multiple timed reagent additions can be made is not easily implemented in micro-format or in an array. Such a complex format however becomes feasible when implemented using integral fluidic i/o devices of this invention. It now becomes possible to inject into a micro-reactor in sequence nucleotide bases contained in four integral fluidic injectors each containing a different base. Incorporation of a base releases PPi which can be detected in the assay mix containing ATP sulphurylase and luciferase when the bioluminescent reaction is triggered by the injection of luciferin from a fifth integral fluidic input.

Another complex reaction format is the family of exquisitively sensitive enzyme amplified bioluminescence assays. This family of methods uses the enzymatic production of a bioluminescent substrate which is then converted to light output through a bioluminescence reaction as known in the art (see J. Bioluminescence and Chemiluminescence, 4, 119–128, 1989). One important example of this method uses the alkaline phosphatase catalyzed conversion of luciferin phosphate to luciferin which then bioluminesces in the presence of luciferase and ATP. The reaction sequence is $$\text{luciferin-phosphate} \xrightarrow{\text{alkaline-phosphatase}} \text{luciferin}$$

$$\text{luciferin} + ATP + O_2 \xrightarrow{\text{luciferase}} AMP + PPi + \text{oxyluciferin} + CO_2 + \text{light}$$

In this method the alkaline phosphatase to be assayed is added to an assay mix containing luciferin phosphate, ATP and luciferase. In this one step assay format the amount of alkaline phosphatase is proportional to the rate of light production or glow intensity. The alkaline phosphatase may be incorporated into a ligand-binding complex as a label in a heterogeneous binding assay as previously described.

A two-step variant of this assay is potentially even more sensitive. In the two-step method practiced using devices according to this invention, the alkaline phosphatase to be assayed is in one or more micro-reactors at one or more micro-locations of an array. The alkaline phosphatase enzyme at a micro-location is either in solution or it is a label contained in a ligand-binding complex of a heterogeneous binding assay. In a first step, luciferin phosphate is added in-situ by a fluidic i/o device of this invention. After an incubation period, in a second step the bioluminescence reaction is triggered by in-situ addition of either ATP or luciferase or both to the assay mix using an integral fluidic i/o device of this invention. At low concentration of alkaline phosphatase the one-step method gives a continuous low level of light glow which may not be discernible from background noise in the light detector. The two step method however permits the build-up of the concentration of the luciferin formed in the alkaline phosphatase-catalyzed first reaction step over the incubation time, which then is followed by a much higher light intensity over a shorter period of time when the luciferin is consumed in the bioluminescence reaction after it is triggered by addition of ATP or luciferase or both to the reaction mixture in the second step. The added complexity of the two-step method and the requirement for rapid injection technology has prohibited the routine use of this method even in single-assay format and it is much too complex to perform on micro-arrays of the existing art. However this assay is particulary suited to implementation using the fluidic i/o devices of this invention.

Site Specific Assays

In another preferred embodiment of the device in accordance with the invention, each micro-location includes micro-reactors with adjacent enclosed hydrophilic matrix circuits providing integral nano-fluidic i/o. In this embodiment the integral nano-fluidic i/o can be used to achieve location specific reaction conditions. The concentration of one or more chemicals introduced into the micro-reaction site can be controlled by the instrument during the assay procedure. This now allows dose response titrations, and fast transient measurement after a concentration step change, as well as site specific control of other chemicals. Control of the multi-pump array is through passive matrix addressing of the electro-kinetic pump electrode array, in a fashion similar to matrix addressing of planar display devices of the known art. One preferred method of control of the reaction condition at each micro-location uses feedback control. In such a scheme a micro-reactor at each micro-location is connected to an enclosed hydrophilic matrix circuit providing one or more independently pumped fluid inputs supplying reagent or sample solutions from enclosed reservoirs to the reactor. Each independently pumped reservoir contains chemicals necessary to be supplied to the micro-reactor in a controlled way, and a label molecule. The concentration of a particular label molecule in the micro-reactor indicates the amount of material pumped from an adjacent reservoir containing the label into the micro-reactor. Measurement probes track the concentration of reaction chemicals and labels in the micro-reactor. The concentration of labels is fed back to control the pump from the reservoir containing the label. In a preferred embodiment the micro-reactor array is optically scanned as would be the case when the assay reaction produces a fluorescent or a luminescent signal. In this case the pump-controlling label molecule also is light emitting so that it can be measured by the same optical scan system used for the assay. Each reagent reservoir contains its own light emitting label, each label emitting at its own different wavelength that is also different from the wavelengths emitted by the light emitting molecules involved in the assay reaction.

High Sensitivity Cellular Assays

In one preferred embodiment of the device in accordance with the invention, each micro-location includes a micro-reactor with adjacent integral fluidic i/o wherein the micro-reactor contains one or a small number of cells or cell lysate. The integral fluidic i/o enables controlled additions of reagent to the reaction micro-volume in-situ to the reaction micro-volume for the study of single cell reactions or the high sensitivity assay of cellular components or chemicals expelled from the cell.

One particularly suitable cellular assay for use with the integral fluidic i/o of this invention is the reporter gene assay known in the art, an example of which is the luciferase reporter gene assay (see for examples J. Bioluminescence and Chemiluminescence, 8, 267–291, 1993). It is possible to test an isolated DNA sequence for its ability to control gene expression by combining it to the coding region of a reporter gene. In this assay the amount of expressed luciferase enzyme is assayed using the enzyme's bioluminescent catalysis of the reaction of luciferin with ATP. One or a number of cells or cell lysate being investigated for the regulation by a particular DNA sequence are introduced into a micro-reactor at a micro-location. Cells are exposed to a particular test substance capable of affecting regulation by the DNA sequence under investigation. The test substance is preferably provided to the micro-reactor in-situ by a fluidic i/o device of this invention. The luciferase reporter gene is expressed when the DNA sequence under study triggers its expression. The assay of luciferase is initiated in-situ by the addition to the micro-reactor of luciferin, ATP or both from an integral fluidic i/o device of this invention.

BRIEF DESCRIPTION OF THE DRAWINGS

Preferred embodiments of the invention will be described in more detail below and with reference to the enclosed drawings, wherein FIG. 1A

DETAILED DESCRIPTION OF THE INVENTION

Figure 1A:
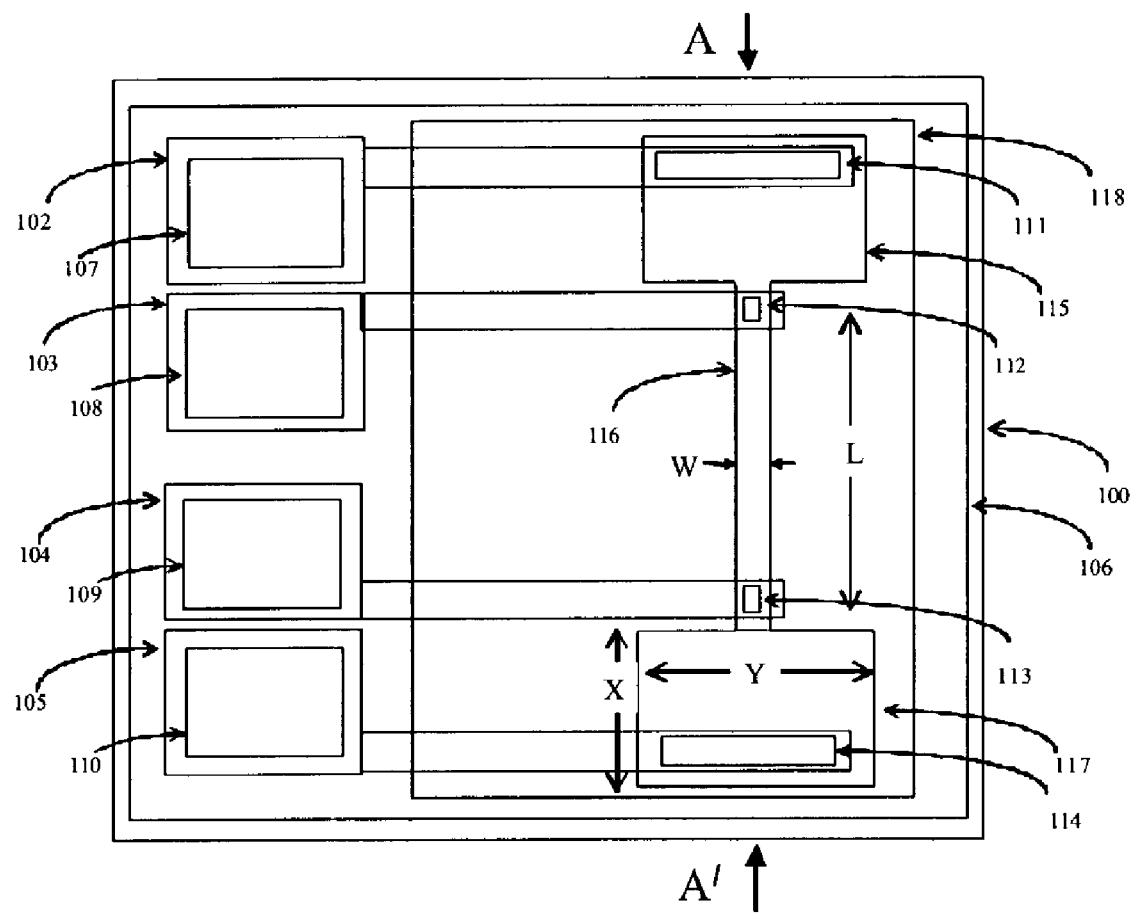
FIG. 1B shows an enclosed hydrophilic matrix device produced in thin film micro-fabrication technology.

In the most general construction, a preferred hydrophilic matrix device of the invention or transport of an aqueous solute includes an insulating substrate 100 (see FIG. 1), a pair of electrodes 103, 104 on the substrate 100, a hydrophilic matrix path 116 on the substrate 100 for electro-kinetic transport of the solute, a water vapor permeable insulator 118 enclosing the matrix and sealing the matrix between the insulator 118 and the substrate 100, and an orifice (not shown) in the insulator above the matrix for the passage of an aqueous solute through the insulator to and from the matrix (see uncovered end 204 in FIG. 2) The insulator material is substantially impermeable to the transported species. Each electrode 103, 104 has a contact end 108, 109 for connection to an external circuit for supplying power and a matrix end 112, 113 for electric contact with the matrix. The matrix ends 112, 113 can be in direct physical contact with the matrix 116 to achieve an electrical connection or spaced from the matrix but sufficiently adjacent thereto for the achievement of an electrical contact with the matrix 116 after wet-up of the matrix. Conductive substances can also be provided between the matrix 116 and the electrodes 103, 104 for the achievement of electrical contact therebetween. The matrix 116 is initially dry and includes a humectant for increasing the water absorption rate of the matrix. Wet-up of the matrix is achieved by exposure of the device to water with water vapor passing through the insulator 118. Water is transported as its vapor through the water vapor permeable insulator 118, into the initially dry, inactive hydrophilic matrix 116. The insulator 118 is otherwise insulating, i.e. it does not transport other solute species, ions or electrons. In the dry state, the matrix 116 is inactive and non-conductive. The matrix is rendered electrically conductive by transferring it into a humidified (wet-up) state by water vapor transport through the insulator 118. The orifice in the insulator 118 can also be used for wet-up of the matrix 116 by capillary action, the vapor permeability of the insulator 118 preventing a pressure build-up in the matrix upon the drawing in of water. The matrix 116 can have a fixed charge for electro-osmotic transport of the solute therethrough. The matrix 116 can also contain a reagent to be electro-kinetically pumped therethrough. Preferably, the reagent is in a dry state when the matrix 116 is in the dry state, in which state the reagent is substantially positionally and chemically stable. The matrix 116 preferably includes an electrolyte salt and the humectant is preferably a neutral molecule. The water vapor-permeable layer may be manufactured from a variety of different materials. Low density, hydrophobic hydrocarbon and fluorocarbon polymers are insulating and water permeable. Silicones, siloxanes, silicone-polycarbonate copolymers are preferred materials because they are insulating and highly water vapor permeable. The most preferred materials are dimethyl polysiloxane and silicone polycarbonate because they can endure a significant physical expansion of the underlying material as water is absorbed.

Although both electrodes and the matrix in the above described embodiment are supported on the same surface of the substrate, it must be emphasized at this point that one or both electrodes can be supported on the opposite face of the substrate, as long as electrical contact between the matrix and the electrodes across the substrate is ensured. This can be achieved by passages or the like through the substrate at the points of contact or by intermediate conductive substances between the matrix and the electrodes. Furthermore, although both electrodes in the above described embodiment are supported on the substrate, the invention encompasses devices wherein only one electrode is supported on the substrate, while the second electrode required for the generation of an electric potential along the matrix path is external to the device. In that situation, electric contact with the second electrode can be achieved through intermediate conductive substances. For example, the second electrode can be located in an electrically conductive fluid coming into contact with the matrix during use of the device.

To better appreciate how the fluidic i/o technology of this invention is practiced we recite below a number of specific examples of enclosed hydrophilic matrix devices that we have made in accordance with the invention.

We have fabricated hydrophilic matrix devices and circuits in thin film micro-fabrication technology and also in combined thin and thick film technology.

Thin Film Enclosed Hydrophilic Matrix Devices

Figure 1B:
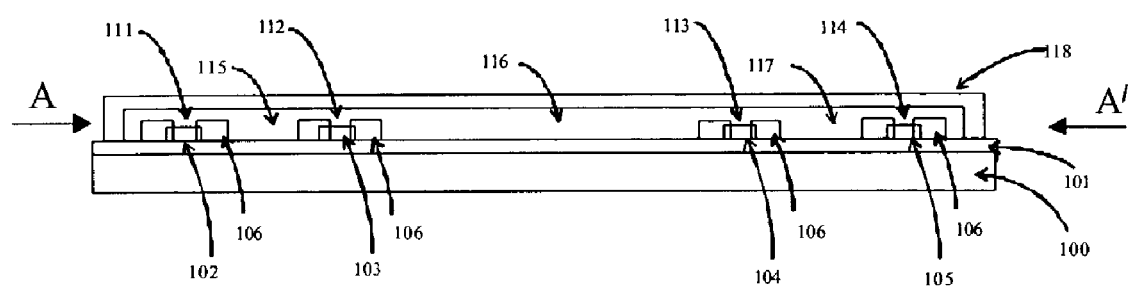

We fabricated the device shown in FIG. 1 in thin film technology for use in testing various component materials and their transport properties. These thin film enclosed hydrophilic matrix devices were fabricated on standard 4-inch diameter polished silicon wafers.

A silicon substrate 100 was first oxidized to give a 1 micrometer insulating silicon dioxide layer 101. Films of titanium (0.015 micrometers thickness) and gold (0.2 micrometers thickness) were e-beam deposited and lithographically patterned to form 4 metal elements: outer metal elements 102, 105 and inner metal elements 103 and 104. Each metal element has one end with a contact pad for connection to an external circuit and the other end for contact to the hydrophilic matrix. Metal elements were coated with an insulating layer 106 and contact pad openings 107, 108, 109, 110 and electrode openings 111, 112, 113, 114 were formed lithographically. Two insulating materials and methods have been used. Firstly, the insulating layer 106 was a commercially available negative resist polymer (SC-100 Arch Chemical Co.). This resist polymer was a spin-coated poly-isoprene which was patterned and developed as a negative resist by UV lithography. Secondly we used a CVD silicon dioxide which was patterned by subtractive etch using HF etchant and a negative resist mask.

Next a thin film hydrophilic matrix was deposited by spin coating and then patterned using one of two techniques. Firstly by direct photo-forming when the matrix was formulated to be photo-crosslinkable. In this process the hydrophilic matrix was spin-coated and exposed to UV through a photo-mask and developed. Secondly by a subtractive dry etch process using a negative photorestist mask and a dry etch of the hydrophilic matrix in oxygen plasma. In this latter process the spin-coated hydrophilic matrix was coated with a negative photoresist which was then photo-formed and developed. The oxygen plasma removed the hydrophilic matrix film that was not protected by the photoresist mask and also removed the photoresist mask leaving a patterned hydrophilic matrix layer. In this method the hydrophilic matrix must be formulated with components that do not form an ash residue in the plasma etch process.

Two types of hydrophilic matrix materials have been used. Firstly we used nano-porous (pore size varying from 1 to 100 nm) hydrophilic polymer matrixes, primarily poly-vinyl alcohols. These films have been patterned by both direct photo-forming (using photo-sensitive stilbazolium functionalized poly-vinyl alcohol) as well as by negative resist and subtractive dry-etching. Secondly we used microporous (pore size varying between 50 to 5000 nm) cellulose acetates films. In a typical process these films were spin deposited at 1500 rpm from a mixed solvent solution (9% cellulose acetate in acetone 90%/water 10%). During the spin process pores are created in the body of the drying film by a phase inversion process. The film also has a 1 to 2 micron thick outer skin which is not porous. A typical film of this process had a bulk porosity of about 70% with pores about 600 nanometers in diameter. These films were patterned using a negative resist subtractive dry-etch process. In this process a negative resist (2.5 micrometers in thickness) was deposited over the cellulose acetate and photo-patterned. Next the pattern was transferred into the cellulose acetate by dry etching. This dry-etch process was performed in a plasma reactor using an oxygen plasma (60 sccm oxygen flow, 150 watts). The etch rate was about 1 micrometer per minute. In this process the oxygen plasma removes cellulose acetate in regions not protected by negative resist as well as the photo-formed negative resist cap layer, and about the top 3 microns of the cellulose acetate underneath it. The final etched cellulose acetate element is about 7 micrometers in thickness.

The formed hydrophilic matrix had two reservoir regions 115 and 117 (width X, length Y in FIG. 1A) connected by a transport path 116 (width W, length L in FIG. 1A). Outer electrodes 102 and 105 contact reservoirs 115 and 117 through holes 111 and 114 and inner electrodes 103 and 104 contact the path 116 at either end through holes 112 and 113.

Finally a film of insulating, gas permeable membrane material 118 was spin-coated from solution. Thus the hydrophilic matrix becomes entirely enclosed by insulator 118. Gas permeable insulator materials that we used were primarily from the family of highly gas permeable poly-dimethyl siloxane polymers (PDMS) and copolymers of polyimide and poly-dimethyl siloxane (PI-PDMS) although other less permeable materials such as poly-isoprene were also investigated. In a typical process we prepared a 8 micrometer thickness film of PI-PDMS (from Gelest Inc.) by spin-coating from a 20% solution of solids in trichloro-ethylene at 2000 rpm, and a 3 micrometer thickness film by spin-coating from a 10% solution at 1500 rpm.

In use, the region of the device located above the gas permeable insulator enclosing the hydrophilic matrix was immersed in water. The electrical contact region was not immersed in water. Water vapor transporting as its vapor through the gas permeable insulator 118 is incorporated into the hydrophilic matrix. Contact was made to the electrical contact pads by probing through the gas permeable layer.

Thin Film and Combined Thin/Thick Film Hydrophilic Matrix Devices

Figure 2:
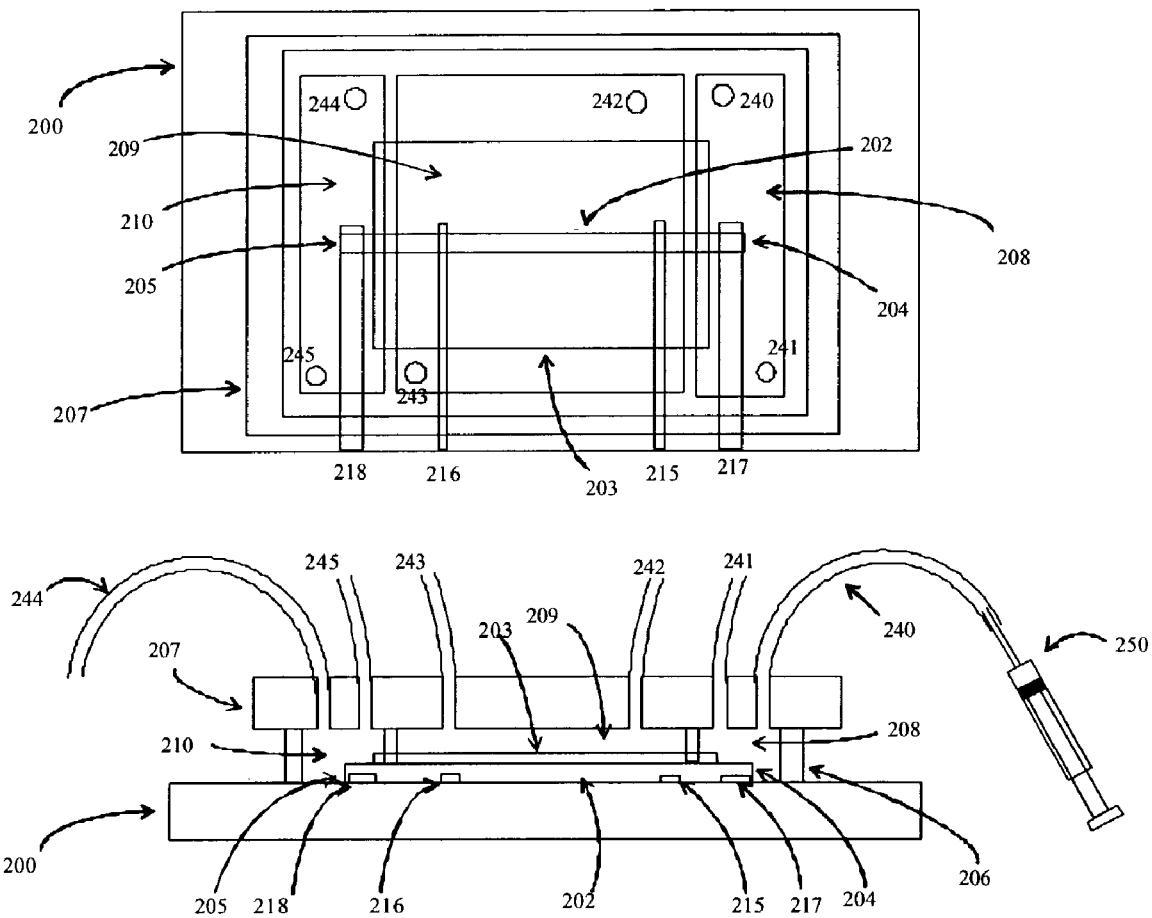
FIG. 2 shows an enclosed hydrophilic matrix device with integral electrodes produced in thick film or combination thin and thick film technology.

We fabricated the device shown in FIG. 2 in thin-film or combination thin and thick film technology. FIG. 2 is one variant of an enclosed hydrophilic matrix device with integral top-side electrodes. In this device there is a planar insulating silicon substrate 200 with four spaced-apart gold electrodes 215, 216, 217 and 218. We used oxidized silicon substrates with gold (deposited and photo-processed as per the recipe for the device of FIG. 1). A hydrophilic matrix transport path 202 with ends 204 and 205 was located so as to contact the four spaced apart electrodes, with end 204 over electrode 217 and in contact with it and end 205 over electrode 218 and in contact with it.

We have investigated both thick and thin film hydrophilic matrix path materials. The thick film element comprised a die-cut hydrophilic matrix path. This element was formed by die-stamping from a sheet (typically 100 to 150 micrometers in thickness and was sized to be narrow (500 micrometers) and have a long dimension (typically about 1 cm) forming the transport path of the electro-kinetic device. The thin film hydrophilic matrix path comprised a spin coated and photo-patterned cellulose acetate using the previously described process.

An enclosing gas permeable insulator coated the hydrophilic matrix transport path along its length. In one version of the device that was used to study the hydrophilic matrix wet-up the gas permeable insulator extended beyond the ends 204 and 205 of the hydrophilic matrix. In this version the hydrophilic matrix was completely enclosed. In another version of the device that was used to study transport properties of previously wetted-up hydrophilic matrixes the gas permeable insulator extended along the hydrophilic matrix path 202 leaving only ends 204 and 205 uncovered.

We have investigated both thick film and thin film gas permeable insulator membranes. The gas permeable insulator was either a 25 micrometer thickness die-cut PDMS element (Adhesives Research) assembled over the hydrophilic matrix path, or a less than 10 micrometers thickness solution-cast PI-PDMS layer applied as a thin film from a 20% solution in trichloroethylene using a stencil process.

The planar substrate and enclosed hydrophilic matrix device was assembled into a micro-fluidic cell comprising three cavities 208, 209 and 210 defined by an elastomer gasket 206 sandwiched between the planar substrate and a co-planar slab of polycarbonate 207.

In the water absorption experiments described below an aqueous fluid was injected into chamber 209 through fluidic pipe 242, and water was incorporated into the initially dry hydrophilic matrix path 202 by vapor transport through the enclosing gas permeable membrane 203. To monitor transconductance of the path during wet-up a voltage can be applied between electrodes 215 and 216 in the transport path 202 to drive current, in which case electrodes 217 and 218 can be connected to electrometers to measure the voltage across the path. Alternatively electrodes 217 and 218 can supply current and 215 and 216 can be used as voltage probes.

In the transport measurements on wetted-up devices fluidic contact to the path 202 was made by injecting an aqueous fluid containing a source chemical to be pumped into chamber 208. Injection was from syringe 250 through fluidic pipe 240. The fluidic contact to 202 occurred at location 204. In some experiments aqueous fluid was also injected into effluent chamber 210, with the fluidic contact to 202 occurring at location 205. The electrode pair in the path 215 and 216 can now be used to supply power to electro-kinetically pump fluid from the source reservoir in chamber 208 to the effluent chamber 210 with electrodes 217 and 218 used as voltage probes or electrodes 217 and 218 can be used to power electro-kinetic flow with 215 and 216 used as probes.

We recite below specific examples of the use of enclosed hydrophilic matrix devices and their performance to further teach how to best practice the invention.

Water Absorption by an Initially Dry Enclosed Hydrophilic Matrix Devices

Both thin film devices of the FIG. 1 configuration and combined thin/thick film devices of the FIG. 2 configuration have been fabricated and their water absorption properties were investigated. We fabricated thin film hydrophilic matrix devices according to the layout of FIG. 1. They comprised poly-isoprene insulated gold electrodes on an oxide coated silicon substrate. We fabricated devices with two kinds of hydrophilic matrixes. One was a micro-porous matrix comprising a dry etched, 7 micrometer thickness micro-porous cellulose acetate layer fabricated as previously described. The other was a nano-porous polyvinyl alcohol. The path dimensions were W=60 micrometers and L=500 micrometers. The reservoirs were X=1.2 mm by Y=2.4 mm. Reagents were introduced into the reservoir by micro-dispensing dissolved reagents onto the reservoir pad. A gas permeable insulator which was a 10 micrometer thick PI-PDMS membrane was applied by spin coating from a 10% solution in trichloroethylene over the hydrophilic matrix.

We measured the channel conductance versus time to characterize the incorporation of water into the enclosed hydrophilic matrix. This was accomplished by applying a voltage to the outer electrodes to drive current from one reservoir to the other through the transport path. The inner electrodes were attached to electrometer voltmeters and probed the iR voltage drop (a standard 4-point probe configuration known in the art) across the transport path. Another external electrode was occasionally immersed in the water to check leakage current through the enclosing gas permeable insulator. As expected, there was no leakage current through the enclosing gas permeable insulator at the normal operating voltages (0–100V) used to drive electrokinetic flow within the device's enclosed hydrophilic matrix path.

Upon initial immersion of the devices into water the path's conductivity was small (typically $10^{-10}$ to $10^{-12}$ ohms$^{-1}$). As water was incorporated into the hydrophilic matrix by permeation of vapor through the gas permeable insulator the conductivity increased and finally became constant when the matrix had fully wet up (typically in the range $10^{-6}$ to $10^{-8}$ ohms$^{-1}$). We found that the rate of water uptake was enhanced by the incorporation of humectants such as hygroscopic salts, low molecular weight poly-ols such as sorbitol and glycerol or other small neutral molecules such as urea or alanine into the initially dry hydrophilic matrix layer. In this disclosure we define humectant to mean any agent whose property is that it draws water vapor to itself. Other terms of the art such as moisturizer and desiccant have similar meaning. The time for water up-take for a device of the above dimensions was greater than 60 minutes for a cellulose acetate matrix without additives but 5 minutes when 20% by weight sorbitol was added to the hydrophilic matrix.

Water uptake through the water vapor permeable insulator into the initially dry micro-porous cellulose acetate hydrophilic matrix caused no appreciable change in the dimensions of the layer. We only observed a change in appearance, as the initially white opaque cellulose acetate became translucent upon water uptake. The initially dry micro-porous cellulose acetate contains about 70% of its volume of air. As water is introduced either the internal air is pressurized or it escapes by permeation out through the enclosing gas permeable insulator. The cellulose acetate remains dimensionally stable. Hydrophilic matrixes comprising porous, low density materials containing appreciable air and which are dimensionally stable during wet-up are preferred materials for use in this invention. The exemplar cellulose acetate is but one of numerous materials of this type that could be successfully employed in the invented devices. Other examples include cellulose nitrate and silica sol-gels made as dimensionally stable porous materials by phase inversion when cast from mixed solvents, materials rendered microporous by templating techniques where a heterogeneous matrix is deposited with an included other material which is subsequently removed by vaporization, a micro-porous material made by casting a suspension of micro-spheres and the like.

Water uptake into the nano-porous PVA was accompanied by significant swelling of the matrix. The initially dry matrix is dense and contains little occluded air. Water uptake causes significant swelling of the volume, up to five fold in some cases. These observations are in line with well known swelling behavior of gel type matrixes. Numerous examples of swellable gels such as the exemplar polyvinyl alcohol are known in the art and will have a similar behavior. These other examples include but are not limited to agarose, poly-acrylamide and poly-hydroxyethyl methacrylate.

An enclosed hydrophilic matrix device of this invention using swellable gel matrixes is less preferred because it requires that the enclosing gas permeable insulator also be elastic so that it can stretch to accommodate the increase in volume that the hydrophilic matrix undergoes upon wet-up. When using swellable gels we have found that it is preferable to use thin hydrophilic matrix layers to limit the absolute amount of swelling. We prefer dry films to be less than 5 micrometers in thickness and even better 1 micrometer.

We performed further water absorption studies on combined thin/thick film and thin film hydrophilic matrix devices made according to the layout of FIG. 2, (with the modification to FIG. 2 that the gas permeable insulator extended over the entire hydrophilic matrix which was thus entirely enclosed as in the device of FIG. 1). The substrate was oxidized silicon with photo-patterned gold electrodes. For the thick film device the hydrophilic matrix transport path was a die cut micro-porous element 150 micrometers thick and 500 micrometers wide by 1.1 cm long. The path element was cut from a cellulose nitrate/cellulose acetate (CA/CN) disc (MF-Millipore). The path element had been soaked in a solution containing humectant and 2 mM phosphate buffer salts and dried. For the thin film device the hydrophilic matrix transport path was a photo-patterned 7 micrometer thick layer of cellulose acetate cast from an acetone/water mixed solvent, impregnated with humectant and 2 mM ammonium phosphate buffer at pH 7. The impregnation step was performed after the cellulose acetate layer has been capped with photo-formed negative resist, then lighly dry-etched to remove the compact skin layer of the cellulose acetate, thus allowing transport of impregnant into the pores. The final step was dry-etching of the cellulose acetate and resist cap as previously described. All chemicals used to impregnate cellulose acetate in this way must be dry-etchable leaving no ash. The above recited neutral humectants (urea, sorbitol, alanine glycerol are all dry-etchable without residue). Other additives that are added before the dry etch process also must be etchable without residue. Thus we have avoided metal ion salts, metal ion surfactants and metal ion buffers because these leave an ash residue in oxygen plasma processing. We have used ammonium salts in their place because they generally etch without residue.

The hydrophilic matrix was enclosed by either a 25 micrometer thickness PDMS layer assembled as a die cut element or a thin PI-PDMS cast from solution through a stencil. The gas permeable insulator element was located over the substrate, electrodes and path entirely enclosing the hydrophilic matrix. The devices were assembled into the micro-fluidic flow cell and water was introduced into the central chamber 209 of the cell. The hydrophilic matrix path absorbed water by vapor transport through the enclosing gas permeable insulator insulator. The conductivity versus time was measured by applying a pulsatile +/−5V across electrodes 215 and 216 and measuring the conduction current versus time.

The dry hydrophilic matrix 202 of the above described devices has an initial internal water vapor pressure lower than the saturated water vapor pressure of the external aqueous solution in the chamber 209 of the fluidic cell. The driving force for water uptake by the enclosed hydrophilic matrix is this water vapor pressure difference. The water flux into the hydrophilic matrix is determined by the gas permeable insulator's permeability times the pressure difference across it. The pressure difference versus time is determined by the internal water vapor pressure versus time. This in turn is determined by the amount of water absorbed into the hydrophilic matrix versus time, and the water vapor absorption isotherm of the hydrophilic matrix materials which might also include humectants and salts. The isotherm relates the amount of water absorbed to the water vapor pressure. As is known in the art the water vapor pressure of an aqueous solution of a dissolved chemical is dependant on the activity of water in the solution which in turn depends on the mole fraction of the dissolved chemical. Certain chemicals which interact strongly with water when in concentrated solutions lower the water vapor pressure significantly relative to the water vapor pressure of pure water. The relationship between water vapor pressure and concentration of dissolved chemicals are well known and tabulated in numerous books on the properties of aqueous solutions (see for example Electrolyte Solutions by Robinson R. A. and Stokes R. H., Butterworths Publications Ltd., 1959). These data form the basis for a model that we have used to predict the rate of water uptake into the enclosed hydrophilic matrixes of this invention. At 100% wet-up the final concentration of the additive humectant in the aqueous compartment of the hydrophilic matrix is determined by the total dry amount initially loaded into the dry matrix. When the additive is incorporated by a soak process the amount to be loaded is determined by the concentration of the original soak-solution.

In Table 1 we have summarized the wet-up data for various devices with different combinations of hydrophilic matrix thickness and gas permeable membrane thickness, and different amounts of humectant.

TABLE 1

| Gas permeable membrane thickness | Hydrophilic matrix thickness | Amount of humectant | T° C. | t(100%) gravimetric | t(100%) conductivity | t(100%) model |
| --- | --- | --- | --- | --- | --- | --- |
| 10 um PDMS | 10 um CA | None | 23 | | >3600 | |
| 3 um PI-PDMS | 7 um CA | 2 M urea | 25 | | 400 | 600 |
| | | 1.7 M sorbitol | 23 | | 700 | 1189 |
| | | 1.7 M glycerol | 23 | | 300 | |
| | | 3 M CaCl2 | 23 | | 200 | 307 |
| | | 3 M CaCl2 | 50 | | 60 | 64 |
| 25 um PDMS | 7 um CA | 2 M urea | 50 | | 575 | 671 |
| 25 um PDMS | 7 um CA | 2 M urea | 25 | | 1000 | 1750 |

TABLE 1-continued

|  |  |  | t(50%) gravimetric | t(50%) conductivity | t(50%) model |
|---|---|---|---|---|---|
| 25 um PDMS | 150 um CA/CN | 40 g/L CaCl2 | 23 | 20,000 |  | 22,000 |
|  |  | 40 g/L CaCl2 | 50 | 5000 |  | 6500 |
|  |  | 8 M urea | 23 | 9,700 |  | 10,300 |
|  |  | 8 M urea | 50 |  | 1750 | 4740 |

We have measured water uptake by gravimetry (difference of the weight of the device before and after wet-up) and by the conductivity change. We have tabulated the time to complete wet up, t(100%), as well as the time to achieve 50% water incorporation, t(50%), (50% weight change or 50% conductivity change). We have also tabulated the wet-up times we calculated from the model of water absorption kinetics described below.

The experimental data and the model show that the time to incorporate water into the hydrophilic matrix is decreased as the humectant loading is increased. However, too large a loading compromises the electro-kinetic function of the wetted-up hydrophilic matrix. When electrolyte salts are used as humectants the final concentration of salt consistent with a usefully short wet-up time (<3600 seconds) is large (>100 mM). Large ionic strength (I) supporting electrolytes suppress electro-kinetic mobility at a rate that scales with $I^{-0.5}$, as is known in the art. Also the high electrical conduction through the electro-kinetic transport paths may cause joule heating and also significantly increases the polarization of the electrodes and risks gas evolution at the electrodes. Thus electrolyte salts are not preferred as humectants. Neutral humectant additives increase the final viscosity of the electro-kinetic medium. However, the loading of many neutral additives at a level that is consistent with rapid wet-up times does not significantly increase the viscosity of the transport medium nor diminish the electro-kinetic mobility. For example sorbitol at 2M, urea at 8M, glycerol at 4M all give rapid wet-up and reduce the electro-kinetic flow by less than 2 relative to an aqueous medium with viscosity of 1. However, concentrated urea solutions denature proteins and nucleic acids as is known in the art. Therefore, urea should be avoided in applications when pumping of proteins or nucleic acids is required under non-denaturing conditions.

We found that the time taken to incorporate water was directly related to the product of the thickness of the gas permeable insulator and the thickness of the hydrophilic matrix. The speed of water uptake increased with the water vapor permeability of the enclosing gas permeable membrane. The experimental wet-up times are consistent with our water absorption model using the published water vapor permeability of PDMS of about $5\times10^{-6}$ $cm^3$ of water vapor. cm (barrier thickness) $sec^{-1}$ $cm^{-2}$ (area) cm $Hg^{-1}$ (pressure difference). The water absorption model predicts the time (t, seconds) to 100% wet-up at temperature T° C. of an enclosed hydrophilic matrix device comprising a hydrophilic matrix of thickness $d_{um\ HM}$, micrometers and $P_{HM}$ terminal fractional water volume (porosity) and an enclosing gas permeable insulator of thickness $d_{um\ GPI}$, micrometers containing a terminal molarity of a humectant M moles/L water according to $$t=A\ P_{HM} d_{um\ GPI} d_{um\ HM} M^{-B} e^{-0.052(T-25)}$$

where A and B are constants depending on the particular humectant and the gas permeable insulator. For a gas permeable insulator comprising PDMS we obtain the tabulated values for the constants A and B

TABLE 2

| humectant | A | B |
|---|---|---|
| Calcium chloride | 10 | 1.23 |
| Ammonium nitrate | 18 | 1.01 |
| Alanine | 26 | 0.97 |
| Glycerol | 28 | 0.95 |
| Sorbitol | 28 | 0.98 |
| Urea | 35 | 0.8 |

For PI-PDMS copolymer membranes the water vapor permeability is about half of PDMS and the wet-up times are thus about twice as long. The neutral humectants shown in Table 2 have similar behavior. For these neutral humectants at a terminal molarity of 2M in a hydrophilic matrix of typical porosity (75%) the time to wet-up through PDMS is approximately 10 $d_{um\ HM}$ $d_{um\ GPI}$ seconds at 25 C. and 3 $d_{um\ HM}$ $d_{um\ GPI}$ seconds at 50 C. The approximate wet-up times for devices with 2M neutral humectant with different thicknesses are shown in Table 3 below.

TABLE 3

| $d_{um\ PDMS}$ | $d_{um\ HM}$ | 25 C. | 50 C. |
|---|---|---|---|
| 1 | 1 | 10 secs | 3 secs |
| 5 | 5 | 4 mins | 80 secs |
| 10 | 10 | 17 mins | 5 mins |
| 25 | 10 | 42 mins | 14 mins |
| 25 | 25 | 104 mins | 34 mins |
| 10 | 50 | 83 mins | 27 mins |
| 25 | 150 | 10 hours | 3 hours |

In summary, thin film (d<10 micrometers) enclosed hydrophilic matrix devices and circuits of this invention can be wet up rapidly in-situ. Thick film devices generally must be wet-up prior to use and often require elevated wet-up temperature. Accordingly we prefer to fabricate devices with hydrophilic matrixes less than 50 micrometers in thickness and gas permeable insulators less than 10 micrometers in thickness.

Electro-kinetic Transport in Wetted-up Enclosed Hydrophilic Matrix Transport Paths.

We used the configuration of FIG. 2 to study the transport properties of hydrophilic matrix materials after wet-up. A candidate hydrophilic matrix material was fabricated into a transport path on a planar substrate, treated according to recipes laid out in Table 4, then further processed to form an enclosed hydrophilic matrix device on the planar substrate as shown in FIG. 2.

The planar device was wet up either by first immersion of the planar substrate in water then assembly into the micro-fluidic cell or by first assembly into the micro-fluidic flow cell and then wet up by introducing aqueous fluids into all of the chambers of the flow cell. We observed wet-up by both incorporation of water through the gas permeable membrane and also by capillary flow from the exposed ends of the hydrophilic matrix path. The device also wets-up by capillary flow when, 1: the hydrophilic matrix is a micro-porous material with surface wetting properties such as a cellulose nitrate or a cellulose nitrate/acetate blend and, 2: fluid is introduced first into one or both the two outer chambers, thus contacting the enclosed hydrophilic matrix at the orifice through the enclosing insulator at its end.. When fluid is introduced into all three chambers simultaneously wet-up of the hydrophilic matrix occurs by both water permeation through the enclosing insulator and by capillary flow through the orifice through the enclosing insulator. In those embodiments of the invented enclosed hydrophilic matrix devices where 1: the material is incapable of capillary flow or, 2: there is an air gap initially separating the enclosed hydrophilic matrix and the bathing fluid and there is no initial contact between the matrix and the bathing fluid above the orifice in the enclosing insulator, then the only path for wet-up is by permeation through the enclosing insulator. The complete wet-up by capillary flow of an enclosed hydrophilic matrix device with only one orifice, (such as described in the injector device described below) requires a vent path for the air contained in the initially dry micro-porous hydrophilic matrix. Such venting occurs by permeation of air out through the enclosing gas permeable insulator. When the enclosing insulator is not gas permeable the amount of water uptake by capillary flow is limited because the internal air is pressurized and has nowhere to escape as water flows in.

one experiment we powered the electrode 217 in the source chamber and grounded the electrode 218 in the effluent chamber 209. In another experiment we powered the electrode 217 and grounded the electrode 216 in the transport path near to the effluent end. We used a number of different techniques to visualize flow. In one experiment we started with the effluent chamber empty then applied power to the source chamber electrode 217 and grounded path electrode 216 and observed aqueous fluid appearing in the effluent chamber. In this experiment we can quantify the electro-osmotic flow of the pumped fluid. In other experiments we added dye to the source chamber and visually observed its rate of transit along the transport path during electro-kinetic pumping. Since the dye molecules are charged, this type of experiment allowed us to quantify the net combined electro-osmotic and electrophoretic transport. In a third type of experiment we started pumping a first electrolyte with a first conductivity from the source chamber until it completely filled the transport path and we measured the transport path conductivity. Then we introduced a second electrolyte with a different conductivity into the source chamber and measured the time for the conductivity of the transport path to achieve a new conductivity as the second electrolyte replaced the first electrolyte by electro-osmotic flow in the transport path. In these experiments we could quantify electro-osmotic flow rate. A detailed description of the conductivity transient method is given by Ren et al. in Journal of Colloid and Interface Science, 250, 238–242, 2002. Combining the dye visualization and conductivity transient experiment permitted simultaneous measurement of electro-osmosis and electrophoresis. We have summarized experimental data in Table 4.

TABLE 4

| Device | Hydrophillic matrix | thickness µm | Wafer level soak treatment | Gas permeable membrane | thickness µm | Source electrolyte composition | Experiment | $\mu_{eff}$ cm$^2$/Vs | $\mu_{eo}$ cm$^2$/Vs | $\mu_{ep}$ cm$^2$/Vs |
|---|---|---|---|---|---|---|---|---|---|---|
| 1 | CA/CN | 150 | 8M urea, 110 mM ADS, 2 mM phosphate buffer @ pH 7 | PDMS | 25 | 2mM phosphate buffer pH 7 | volumetric | — | $-1 \times 10^4$ | — |
| 2 | CA/CN | 150 | none | PDMS | 25 | 10 mM phosphate buffer pH 7.2 10 mM Allura red dye | anionic red dye | $2.2 \times 10^4$ | $-8 \times 10^5$ | $3.1 \times 10^4$ |
| 3 | CA/CN | 150 | 2.3 mM TX-100 | PDMS | 25 | 10 mM phosphate buffer pH 7.2 10 mM Allura red dye | anionic red dye | $3.1 \times 10^4$ | 0 | $3.1 \times 10^4$ |
| 4 | CA/CN | 150 | 11 mM ADS | PDMS | 25 | 10 mM phosphate buffer pH 7.2 10 mM Allura red dye | anionic red dye | $-8 \times 10^5$ | $-3.9 \times 10^4$ | $3.1 \times 10^4$ |
| 5 | CA/CN | 150 | 2.3 mM TX-100 | PDMS | 25 | Soln 1:50 mM phosphate pH 7.2 5 mM Allura red dye Soln 2:55 mM phosphate pH 7.2 | anionic red dye + conductivity | $2.2 \times 10^4$ | 0 | $2.2 \times 10^4$ |
| 6 | CA/CN | 150 | 110 mM ADS | PDMS | 25 | Soln 1:50 mM phosphate pH 7.2 5 mM Allura red dye Soln 2:55 mM phosphate pH 7.2 | anionic red dye + conductivity | $3 \times 10^{-5}$ | $-2.2 \times 10^4$ | $2.5 \times 10^4$ |
| 7 | CA | 7 | none | | | Soln 1:50 mM phosphate pH 7.2 5 mM Allura red dye Soln 2:55 mM phosphate pH 7.2 | conductivity | — | $-5.3 \times 10^5$ | — |

In electro-kinetic transport experiments on wetted-up devices shown in FIG. 2 we first introduce an electrolyte to be pumped into the source chamber 208 and then applied a voltage across the transport path in one of several ways. In In this table we show the direction of transport with respect to a negative source electrode. The effective electro-kinetic mobility $\mu_{eff}$ is the sum of the electrophoretic $\mu_{ep}$ and electro-osmotic $\mu_{eo}$ mobilities. A positive (negative) mobility indicates flow away from (towards) the negative source electrode due to electrophoresis of an anion (cation) or electro-osmosis created by a fixed positive (negative) surface charge and a negative (positive) space charge.

EXPERIMENT i:

We evaluated device number 1 of Table 4. An aqueous solution of 2 mM phosphate buffer was introduced into chamber 208, water into central chamber 209 and the effluent chamber 210 was initially empty. A voltage was applied between large electrode 217 (which contacted the hydrophilic matrix path close to source chamber 208) and electrode 216 which contacted the hydrophilic matrix in the transport path with a contact of 500 micrometer×500 micrometer dimensions. The applied voltage provided the power to drive electro-kinetic flow of electrolyte along the path. Electrodes 215 and 218 were connected to electrometers to probe the voltage at different locations along the path. When the applied voltage was at +10V on 217 relative to 0V at 216 (the voltage drop across the transport path was 6V), electrode 316 polarization was 1.5V, electrode 317 polarization was 0.5 V and the current was 2 micro-amps. There was fluid flow along the path from the filled source chamber 208 into the initially empty effluent chamber 210. The amount of fluid collected into the empty effluent chamber 210 versus time was estimated volumetrically by monitoring the diameter of the formed water drop versus time. We estimated 0.1 micro-liters per second at 6V for this pump. This resulted in an estimated electro-osmotic mobility of about $1 \times 10^{-4}$ cm$^2$/Vs away from the positive source electrode to the effluent chamber.

Note that the hydrophilic matrix path comprises an electro-kinetic pumping zone between power electrodes 217 in the source chamber and 216 in the transport path, and a zone between power electrode 216 and the effluent chamber 210 through which fluid flows with resistance but where there is no applied voltage. In the parlance of micro-fluidics this would be called a load. This arrangement is advantageous because the effluent chamber need not be electrically connected to the pump power source and hence it can be supplied by multiple independently powered pumps configured as the one described here. Also it is now possible to connect an enclosed hydrophilic matrix pump upstream of a reservoir containing the material to be pumped. In this arrangement there is a pumping region comprising a source reservoir containing pump electrolyte fluidically connected to an enclosed hydrophilic matrix transport path. There is a first pumping electrode in the source reservoir or in the path close to the source reservoir and a second pumping electrode in the transport path. The path is further fluidically connected beyond the second pumping electrode to an enclosed hydrophilic matrix second reservoir containing a species to be pumped. The second reservoir is fluidically connected to the effluent chamber. In the use of the device in this configuration the material in the second reservoir is pushed by the fluid that is electro-osmotically propelled along the path from the first reservoir through the second reservoir into the effluent chamber. The electro-osmotic pump and its power electrodes are thus separated from the material for pumping which resides in a field free region downstream of the pump.

There is a maximum current that the small electrode 216 can supply without evolution of gas bubbles. Gas evolution is deleterious to the stable operation of the pump. For the device with a 500 micrometer wide×150 micrometer thickness transport path with a 500 micrometer×500 micrometer path electrode 216 the observed 2 micro-amps represents approximately the maximum current flow at 216 due to cathodic reduction of dissolved oxygen that can be supported before the electrode cathodically reduced water to hydrogen gas. For a device operating with a small electrode situated in the transport path the maximum pump power is thus determined by the pump's maximum current limited by oxygen reduction. For higher power operation the concentration of the supporting electrolyte can to be lowered (to reduce conduction current), or neutral dissolved oxidant (which can be cathodically reduced at the electrode 216) can be added to the hydrophilic matrix. For a hydrophilic matrix pump with positive fixed charge and positive zeta potential the pumping voltage is the reverse of the above-described. In this case the small path electrode 216 is the anode. Absent redox material added to the hydrophilic matrix the limiting pump current is that provided by the maximum rate of oxygen evolution without gas bubble formation. Again, a current of about 2 micro-amps can be supplied before gas evolution occurs. For higher power operation the concentration of the supporting electrolyte can to be lowered, or neutral dissolved reductant (which can be anodically oxidized at the electrode 216) can be added to the hydrophilic matrix.

It is of advantage for the above described device with the small electrode in the transport path operating as a cathode (anode) by oxygen reduction (evolution) that the enclosing gas permeable insulator that enables wet-up of a dry hydrophilic matrix also is permeable to oxygen. We have calculated that a significantly larger diffusional flux of oxygen to or from the electrode occurs when there is lateral permeation of oxygen through the enclosing gas permeable insulator layer than would occur if the layer was impermeable to oxygen. Thus such a device can support larger pump currents before gas evolution than would otherwise be possible.

It is well known in the art of microelectrodes that as the electrode is scaled down in size more and more of the electrochemical current is supplied by lateral diffusion of the redox molecule to the electrode perimeter. Thus as the device of this invention is scaled down in size the efficiency of the electrodes to deliver current also improves. The relative enhancement of current capacity by lateral transport of oxygen through the gas permeable layer also increases as the device is scaled down in size.

EXPERIMENT ii

We have investigated the use of surfactants to tailor the zeta potential of micro-porous materials. In transport experiments on device 2 of Table 4 we found that untreated micro-porous cellulose acetate/cellulose nitrate matrix has a low zeta potential due to fixed negative charge on the pore surface and some electro-osmotic pumping takes place. We obtained similar results on transport experiments performed on device 7 of the table which comprised solution-cast, micro-porous cellulose acetate.

When we incorporated a non-ionic surfactant such as Triton TX-100 into the hydrophilic matrix (devices 3 and 5 of Table 4) the adsorption of non-ionic surfactant on the pore surface was found to suppress the zeta potential and the micro-porous material becomes less active to electro-osmotic pumping. We observed the fastest flow of anionic red dye by electrophoresis only. Comparing the mobilities observed in the transport experiments on devices 3 and 5 showed lower electrophoretic and electro-osmotic mobility at the higher ionic strength of the run buffer in device 5 versus device 3.

When we incorporated an anionic surfactant such as ammonium dodecyl sulfate (ADS) into the hydrophilic matrix (devices 4 and 6 of Table 4) the pore surface adsorbed charged anions and the micro-porous material becomes more active to electro-osmotic pumping (in the direction away from the positive electrode) and opposite to the anionic dye electrophoresis. The zeta potential of such a treated hydrophilic matrix was estimated in the range −10 to −20 mV. The net effective flow of dye was much slower and even in the opposite direction relative to electrophoresis alone. Comparing the mobilities observed in the transport experiments on devices 4 and 6 showed lower electrophoretic and electro-osmotic mobility at the higher ionic strength of the run buffer in device 6 versus device 4.

Alternatively, as has been previously described in silicon capillary devices (Lucy et al. Anal. Chem. 68(2), 300–305, 1996), when a cationic surfactant such as cetyl trimethyl ammonium chloride (CTAC) is incorporated into the hydrophilic matrix, the, pore surface can adsorb charged cations and the micro-porous material can lose its negative zeta potential and become charge neutral or even mildly positive thus becoming active to electro-osmosis in the direction towards the positive electrode.

We have found it convenient to tailor the surface charge necessary for electro-osmosis by adsorption of surfactants onto the pore surface of the micro-porous hydrophilic matrix. There are many surface active reagents known in the art that will adsorb on a surface to produce or modify a surface charge. Also, there are numerous other methods known in the art that can equally well be used to introduce surface charge. These include chemical methods (see for example Kumar et al., Drug Development and Industrial Pharmacy, 19, 1–31, 1993), surface attachments and derivatization methods (see for example Ma et al., Macromolecules, 33, 331–335, 2000), plasma modification (see for example Poncin-Epaillard et al., J. Appl. Polymer Sci., 44, 1513–1522,1992), physical entrapment of charged entities (see for example Wroblewski et al., Sensors and Actuators, 48, 471–475, 1998) and the like. Any of the methods known in the art can be used to introduce to or modify the surface charge of a micro-porous surface of a hydrophilic matrix device of this invention. As is also known in the art, charged surfaces can cause adsorption of the reagents being transported, particularly when the reagent being transported has a charge opposite to the charge on the pore surface.

In those devices of this invention where the reagent is in the electro-kinetic pumping region of the hydrophilic matrix device and when pumping is by electro-osmosis, the quantity and chemical nature of the surface charge must be sufficient to induce electro-osmotic flow yet not cause significant adsorption of the reagent being transported through the pores. Accordingly in these devices we believe that the optimum treatment to induce surface charge will utilize a method resulting in a surface that minimally adsorbs the reagent to be pumped and this method likely will be particular to the species being transported. In other devices of this invention where the reagent to be pumped is in a separate second reservoir close to the effluent end of the injector and beyond the electro-kinetic pumping region, the surface charge of the pore surface of the pump region can be adjusted with any of the surface treatments recited above without needing to consider the interactions with the reagent to be pumped.

Figure 3:
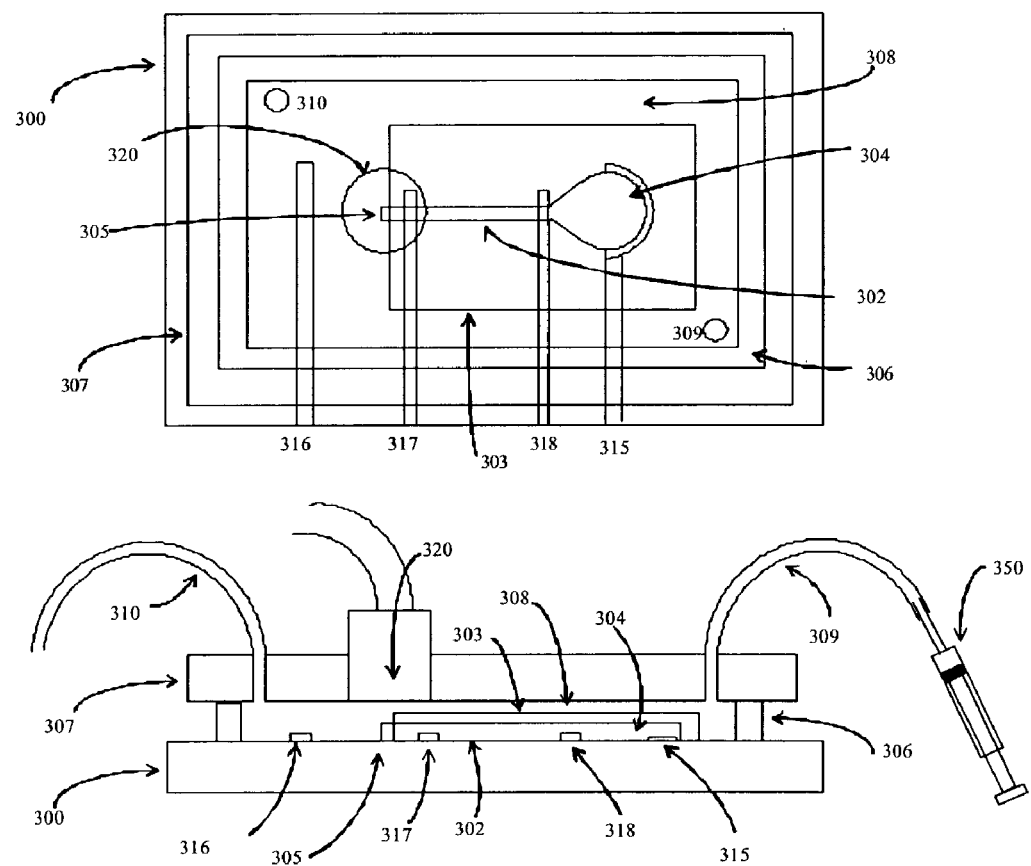
FIG. 3 shows an enclosed hydrophilic matrix device with integral electrodes and integral enclosed reservoir produced in thick film or combination thin and thick film technology.

Fluidic i/o to a Micro-location using an Enclosed Hydrophilic Matrix Injector Comprising Enclosed Transport Path and Reservoir Another embodiment of an enclosed hydrophilic matrix device with integral top-side electrodes is shown in FIG. 3.

The injector-pump device of this example is a basic building block of the micro-reactor array with integral fluidic i/o of this invention.

In this example we fabricated the device on an oxidized silicon substrate. On the substrate were four spaced apart electrodes 315, 316, 317 and 318 which were 0.2 micrometer thick photo-patterned gold fabricated as per the previously described recipe. A 7 micrometer thickness micro-porous cellulose acetate hydrophilic matrix was spin-coated, photo-formed and impregnated as per the previously described process procedures. The impregnation was with reagents shown in Table 5. The micro-porous film including impregnated salts, surfactant and humectant was formed into an element contacting the spaced apart electrodes. At one end of the formed hydrophilic matrix there was a circular reservoir region 304 in contact with a crescent shaped electrode 315 at one side of the reservoir away from its effluent end. The reservoir region was in contact with one end of a transport path region 302 which contacted the electrodes 317 and 318 along its length. The transition from the circular reservoir to the narrow transport path was tapered so as to avoid pressure hot spots during pumping. The transport path 302 had an effluent end 305 beyond the region of its contact with electrode 317. Next we deposited material for pumping into the reservoir region by volumetric dispensing of a known dose of the material dissolved in water as indicated in Table 5. The dose was calculated to give a terminal concentration in the reservoir shown in the table after the micro-porous hydrophilic matrix had fully wet up. Finally the hydrophilic matrix was coated by a gas permeable layer 303. The layer 303 was formed over the hydrophilic matrix enclosing it entirely except at the effluent end of the transport path at 305. Two coating methods were used. In a thin/thick film version of this example we assembled a die cut 25 micrometer thick film of PDMS. In thin/thin film versions of this example we coated a 10 micrometer PI-PDMS through a stencil from a 20% solution in trichloroethylene.

The planar substrate and enclosed hydrophilic matrix device was assembled into a micro-fluidic cell comprising a fluidic chamber 308 defined by an elastomer gasket 306 sandwiched between the planar substrate 300 and a coplanar slab of polycarbonate 307. The chamber was fluidically connected through an inlet pipe 309 and an effluent pipe 310. Aqueous solutions were injected into the chamber by the syringe 350. There was a fiber optic bundle 320 whose one end was located in the polycarbonate slab 307 just above the injector's effluent end 305. The other end of the fiber bundle 320 was connected to a diode light detector (not shown) for light measurement.

We have investigated the pumping properties of the enclosed hydrophilic matrix injector using a model chemiluminescent system. We have used the chemiluminescent reaction

$$\text{Luciferin} + ATP + O_2 \xrightarrow{\text{luciferase}} \text{Oxyluciferin} + AMP + PPi + CO_2 + \text{Light}$$

as our model system. The assay reagents were obtained from Sigma Chemical Co. This model system is useful in a number of inventive embodiments of the invention as previously described.

In one format of this assay we prepared injectors with ATP in their reservoir. Devices were fabricated with 7 micrometer thickness solution-cast cellulose acetate hydrophilic membranes as previously described. Also as previously described there are two process steps in which reagents were added to the matrix. In a first wafer-level soak process the array of patterned hydrophilic matrix structures are exposed to a soak solution to impregnate materials into the entire matrix (reservoir and path). The second process step is performed immediately before enclosing the matrix in the gas permeable insulator. In this process the reagent to be pumped and additional other reagents are deposited from an aqueous solution by a micro-dispense process into the reservoir region. Table 5 summarizes the various recipes that we used in these experimental integral ATP injectors.

After fabrication the injector was assembled into the flow cell as shown in FIG. 3, and an assay mix containing luciferin and the enzyme luciferase was introduced into the fluidic chamber 308 through conduit 309 from syringe 350. The integral fluidic i/o injector wets-up by water absorption through the gas permeable insulator. After wet up the injector device, in its active state, is now capable of injecting ATP into the reaction chamber. ATP was injected from the reservoir into the reactor by applying a voltage to the reservoir electrode 315 with respect to ground. The ground electrode can be in the solution 316 or in the path at one of the path electrodes. The baseline light level was recorded when there was no reaction (absent ATP) and then monitored with time as ATP was injected from the reservoir 304 into the reaction chamber 308.

different amounts of ATP into the reactor and measuring the light output. We performed two kinds of tests. Dose response curves for additions of ATP at constant voltage and varying times and dose response curves for additions of ATP at varying pump voltages.

Figure 4A:
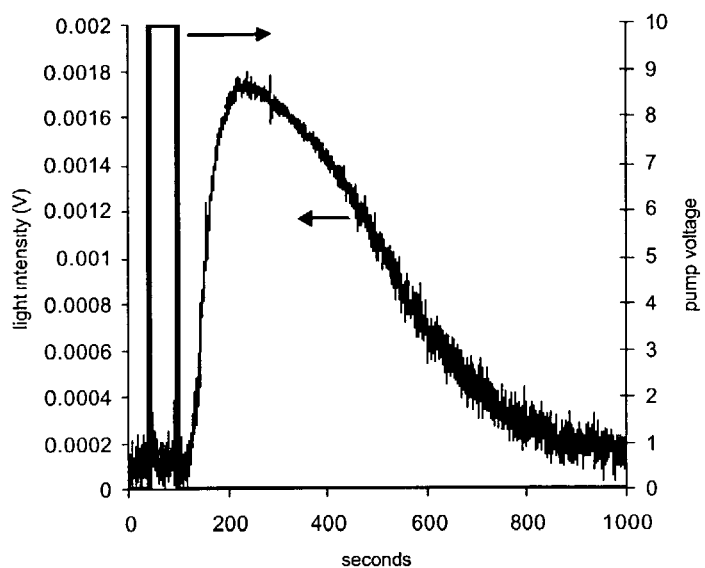
FIG. 4A illustrates chemiluminescent light output versus time for electro-kinetically injected ATP from an integral injector.
Figure 4B:
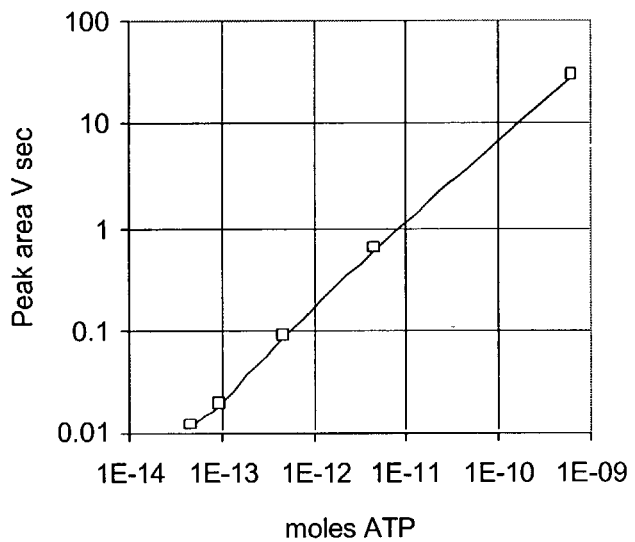
FIG. 4B illustrates a dose response curve for an integral ATP injector.

A dose response curve is shown in the graph of FIG. 4B. The data in this graph were obtained on device number 1 of Table 5. This device was used to inject ATP from a reservoir impregnated with ATP at 100 mM. In this experiment we were able to inject doses of ATP from as low as $10^{-14}$ moles (0.1 pL total injected volume at 100 mM concentration) up to $10^{-9}$ moles (10 nL injected volume at 100 mM concentration). The transport path had been treated by absorption of CTAC cations on the cellulose acetate pore surface. ATP transport was achieved by applying a negative voltage in the range −1 to −10 volts to the reservoir electrode with respect to the ground in the reactor chamber. Electro-kinetic transport was presumably both by electrophoresis and electro-osmosis in the direction along the path from the reservoir to the effluent end of the injector. With −10V applied between electrodes 315 and 316 the linear velocity along path 302 was 22 microns per second along a 3 mm long path with 6.5 volts across it (measured between probe electrodes 317 and 318), resulting in a volumetric pump rate of about 7 pL/sec (for a 65 micrometer wide×7 micrometer thick×70% porosity transport path) and a ATP injection rate of 0.7 pmoles/sec. With −2 V applied the linear velocity was about 2

TABLE 5

| | Wafer level soak | | | | Micro-dispense | | | | |
|---|---|---|---|---|---|---|---|---|---|
| Device | Buffer salt | humectant | surfactant | Redox electrolyte | Pump reagent | Buffer salt | humectant | surfactant | Redox electrolyte |
| 1 | None | 2 M urea | 15 mM CTAC | None | 100 mM ATP | none | 2 M urea | 0.15 mM CTAC | none |
| 2 | None | 2 M urea | TX | None | 10 mM ATP | none | 2 M urea | 0.03% TX | none |
| 3 | 25 mM carbonate | 2 M urea | 110 mM ADS | None | 10 mM ATP | 25 mM carbonate | 2 M urea | 3% ADS | none |

FIG. 4A shows a typical experimental bioluminescent light curve. At the start of the experiment the light level is at baseline. At 40 seconds the reservoir electrode is excited by −10V with respect to ground in the reactor. The voltage is applied for 60 seconds. There is a lag time after the voltage is applied and before the light intensity starts to increase. This is the time to pump ATP along the injector's path from the reservoir to the effluent end. This time lag allows an estimate of the linear pump speed and hence the effective electro-kinetic mobility. If the injector is used for multiple subsequent additions there is no lag time because the pump's path is already primed with ATP. The linear pump speed multiplied by the injector path volume per unit length multiplied by the concentration of ATP in the injector gives the number of moles of ATP being pumped per second. Moles per second of ATP multiplied by the pumping time gives the total dose of ATP injected into the reactor. ATP arriving at the effluent end of the injector's path triggers the bioluminescence reaction with assay reagents in the approximately 1 micro-liter volume of the reaction chamber in the region of the effluent end and directly under the fiber optic light collector.

The area under the light intensity versus time curve is proportional to the total number of moles of ATP converted to light. A dose response curve can be generated by injecting microns per second with 0.6 volts voltage drop across the path, resulting in a volumetric pump rate of 0.7 pL/sec and an ATP injection rate of 70 fmoles/sec. The effective electro-kinetic mobility was $1.04 \times 10^{-4}$ cm$^2$/Vs. The dose response curve was linear over the measured range as shown in FIG. 4B.

Figure 4C:
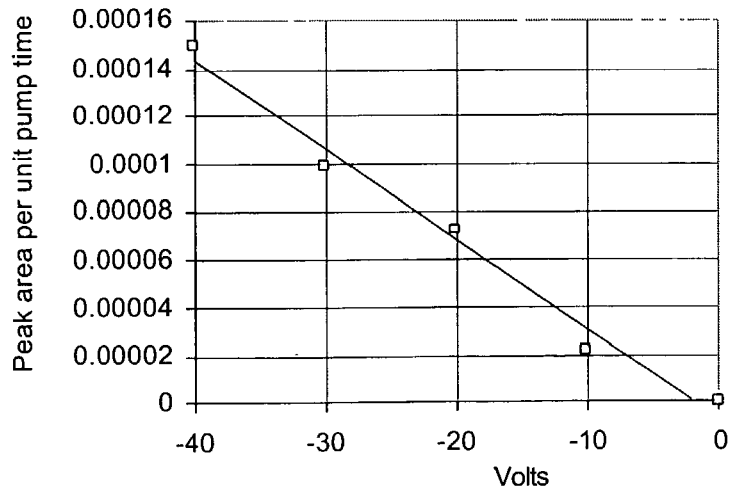
FIG. 4C illustrates the voltage dependence of the pump rate of an integral ATP injector.

In another experiment using device 2 of Table 5 we investigated the voltage dependence of electro-kinetic pumping. The transport path of this device was treated with TX non-ionic surfactant. Therefore we anticipated little of no electro-osmosis. We injected a dose of ATP at a first low cathodic reservoir voltage and recorded the light output. We then injected a second dose of ATP at a second larger cathodic voltage and recorded a second light output. We progressively stepped up the applied voltage to inject larger doses of ATP, measuring light output at each voltage to generate a dose response curve. In FIG. 4C we show the results of this experiment. In this graph we have plotted the light intensity for a given injection divided by the injection time to obtain a pump rate versus applied voltage. The pump speed is linear with applied voltage up to −40 volts. Above −40 volts the amount of light progressively decreased. We believe that at low applied voltages we were measuring predominantly electrophoretically pumped ATP. At above −40 volts there was electro-osmosis in the direction towards the cathode in the reservoir thus reducing the effective ATP efflux rate.

In another experiment we used device 3 of Table 5. The transport path of this device was treated with ADS anionic surfactant. Therefore we anticipated electro-osmosis and electrophoresis to be in opposite directions. We saw no ATP until we applied +100 volts to the reservoir electrode. At this applied voltage we saw a net electro-osmotic efflux of ATP from the injector at 50 fmoles/sec. The effective electro-kinetic mobility was $7 \times 10^{-5}$ cm$^2$/Vs.

The conclusion from the above series of experiments is that the best mode of design of an integral fluidic injector of the FIG. 3 configuration is to tailor the fixed charge within the injector's transport path to be opposite to the charge on the reagent being pumped, so that electrophoresis and electro-osmosis are co-operative. When the pumped reagent is neutral then either sign of fixed charge is acceptable.

The injector configuration described above differs significantly from conventional micro-fluidic arrangements because the source reservoir is entirely enclosed. Since the reservoir is not vented, a back pressure could build up as fluid is electro-kinetically pumped out through the injector's transport path. We have calculated that if the injector's reservoir has rigid dimensions as the reservoir is depleted of a volume of electrolyte, a gaseous volume at a reduced pressure results. As a typical example if the reservoir contained initially 10% air space we can pump 5% of the reservoir volume and achieve a back-pressure of about 0.5 atmospheres. It is thus of significant advantage for the injector of this invention that the gas permeable insulator that enables wet-up of the initially dry hydrophilic matrix also is permeable to air. In this case the back-pressure due to volume displacement by electro-kinetic evacuation of electrolyte from the reservoir will be reduced as air back-fills the reservoir by permeation through the enclosing gas permeable insulator. In our calculations using published values of air permeability of PDMS we have determined that we can achieve the typical electro-kinetic flow without back-pressure build-up because the rate of air influx is always sufficiently high.

It is clearly necessary to design such non-vented enclosed pumps with hydrophilic matrix materials that are capable of providing sufficient electro-kinetic pumping force against back-pressure. In the art of capillary electro-kinetic pumps it is well known that the ability to pump against back-pressure increases as the capillary dimensions are reduced. An open 50 micrometer diameter capillary tube or channel with charged walls as used in conventional lab-on-a-chip micro-fluidics devices has limited capability to pump against back-pressure. A nano-porous material such as nafion can pump against large back-pressure but the pumped volume is small and the electrical current is large. We have found that micro-porous materials with pore diameters ranging from 50 nm to 5 micrometers are suitable and 100 nm to 1 micrometer are preferred for this device design because they can operate against back-pressure and deliver useful pumped volume.

We describe now yet other possible configurations of micro-reactors and fluidic i/o comprising enclosed hydrophilic matrix devices that can be utilized in practical bioassay applications. We recite below in more detail specific inventive fluidic i/o devices utilizing enclosed hydrophilic matrix devices.

Figure 5:
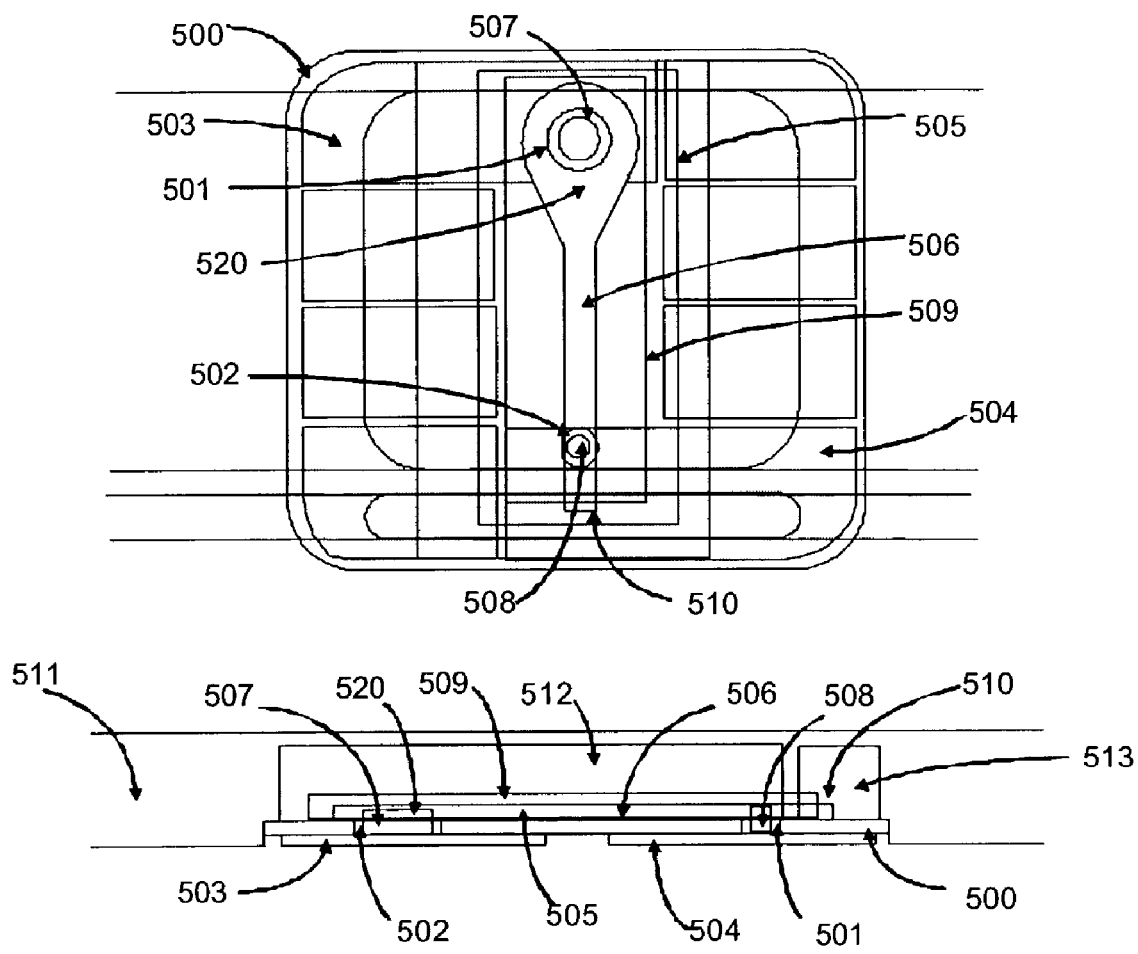
FIG. 5 shows an enclosed hydrophilic matrix device with integral electrodes and through-substrate electrical contact produced in thick film or combination thin and thick film technology.

In FIG. 5 epoxy foil sheets with die stamped holes with laminated metallization such as is used in the manufacture of chip modules for smart cards can be used to fabricate enclosed hydrophilic matrix devices with integral electrodes and back side contacts. The materials and methods for smart-card type laminates have also been described in co-pending application Ser. No. 09/871,823.

An enclosed hydrophilic matrix injector pump with integral back-side electrodes is shown in FIG. 5. In this device there is a planar insulating epoxy substrate foil 500 with holes 501, 502 die-cut through the foil. The under-side had been previously laminated with copper foil which was photo-patterned to form electrode contact elements 503, 504, and then plated with gold. This process is well established in the manufacture of smart-card chip modules, except the lay-out of the punched holes and the contact metal pattern is modified to adapt the technology for use in electro-kinetic devices according to this invention. On the upper side of the epoxy foil there is a hydrophilic matrix formed into a transport path 506 and a reservoir region 520. Hydrophilic matrix components 507 and 508 contact the electrodes 503 and 504 through holes 501 and 502 and also contact the hydrophilic matrix along the path 506 and at the reservoir 520. A layer of gas permeable insulator 509 is coated over the hydrophilic matrix elements 506, 520, 507, 508, thus enclosing the hydrophilic matrix circuit. A region 510 of element 506 is left uncoated. This is the effluent orifice of the enclosed hydrophilic matrix injector pump. The module is sealed into a card-housing 511 comprising fluidic channels 512 and 513. In use aqueous solution for wet-up of the enclosed hydrophilic matrix pump is supplied to channel 512 and reactant solution is supplied to 511. A voltage is applied between electrodes 503 and 504 to propel fluid containing reagent out through orifice 510 into the reactant stream.

FIGS. 6–8 show devices with a micro-location comprising a micro-reaction site and multiple adjacent injectors for supplying integral chemical reagents to the reaction site. The inventor anticipates many possible bioassay formats requiring micro-reactors and multiple adjacent fluidic i/o supplying integral reagents to the micro-reactor. Accordingly the figures describe device configurations demonstrating how to connect more than one integral reagent injector around a micro-reactor. The configurations also show some additional design features enabling a wider range of device performance.

FIG. 6 shows a single micro-location of a planar device comprising at least one and possibly an array of micro-locations.

Figure 6A:
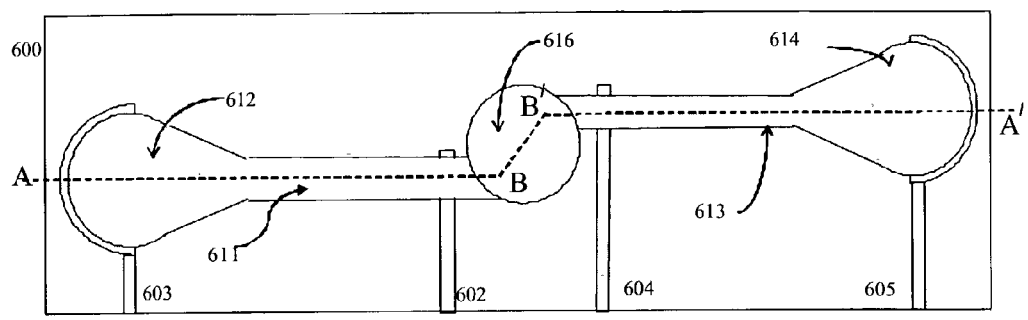
FIG. 6A is a schematic top plan view of a micro-location consisting of a micro-reactor and multiple integral fluidic injectors.
Figure 6B:
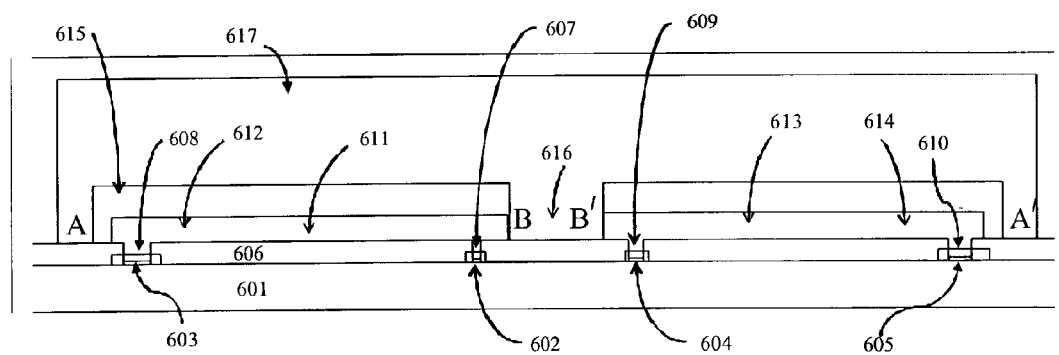
FIG. 6B is a schematic side view of a micro-location consisting of a micro-reactor and multiple integral fluidic injectors.

FIG. 6A is a top view schematic and FIG. 6B is a side view schematic through the cross section ABB'A' of FIG. 6A. There is a micro-location 600 of a planar insulating substrate 601 with four spaced apart electrodes comprising two pumping pairs 602, 603 and 604, 605. There is an insulator 606 on the planar substrate covering the electrodes except at the openings 607, 608, 609 and 610 where contact is made to an overlaying hydrophilic matrix. The electrodes are connected elsewhere on the planar device to an external circuit providing power to the electrodes (not shown).

There are two formed hydrophilic matrix fluidic injectors, each comprising a reservoir and a transport path with one end connected to the reservoir and another effluent end. Each reservoir contains at least one chemical reagent to be pumped and the reagents in each reservoir can be different. The first injector has its reservoir 612 over opening 608 of electrode 603 and its transport path 611 fluidically connecting reservoir 612 to the micro-reactor 616 located at the effluent end B, with electrical contact through opening 607 to electrode 602 close to its effluent end. The second injector has its reservoir 614 over opening 610 of electrode 605 and its transport path 613 fluidically connecting reservoir 614 to the micro-reactor 616 located at the effluent end B', with electrical contact through opening 609 to electrode 604 close to its effluent end. A gas permeable insulator 615 overlays and fully encloses each of the fluidic injectors except at their effluent end where there is an opening at the micro-reactor location 616.

In use of this device the planar micro-location is brought into contact with aqueous fluid (contained for example in a micro-channel 617 shown in FIG. 6B but, equally possible, contained in a micro-well or other conventional fluidic chamber of the art). Water vapor permeates through gas permeable insulator 615 and wets-up the enclosed hydrophilic matrix injectors. The aqueous fluid in the channel 617 or other aqueous fluids subsequently introduced into the channel can contain a sample to be reacted at micro-reactor 616 as well as other reagents. During this time the injectors are fluidically connected to the reactor. Thus there is an opportunity for chemical reagents in the injectors' reservoirs to move into the reactor by diffusion along the transport paths before the injectors are powered by their respective electrodes. When a voltage is applied to 603 and 605 with respect to grounded 602 and 604 there is electro-osmotic propulsion of fluid within the injectors. The fluids being propelled out of the effluent ends of the injectors carries integral reagents contained within the reservoirs of the enclosed hydrophilic matrixes into the reactor. Electro-osmotic transport of reagent along the injectors' transport path is much more rapid than diffusional transport in devices in which the transport paths are longer than 100 micrometers between the reagent reservoir and the micro-reactor. Thus there will be little or no reagent leakage into the micro-reactor until electro-osmotic pump power is supplied.

Figure 7A:
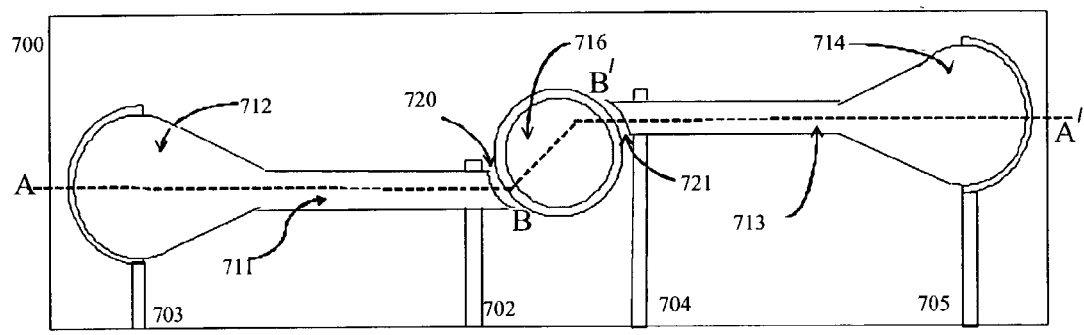
FIG. 7A is a schematic top plan view of a micro-location consisting of a micro-reactor and multiple integral fluidic injectors incorporating diffusion stops.
Figure 7B:
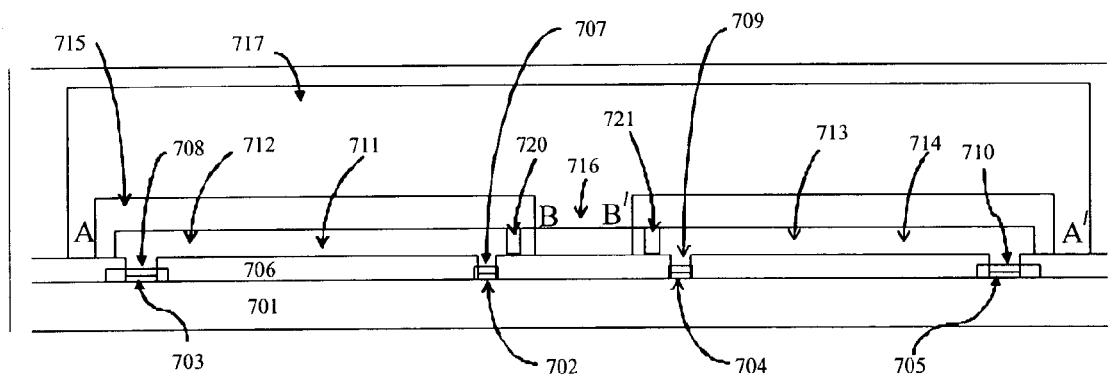
FIG. 7B is a schematic side view of a micro-location consisting of a micro-reactor and multiple integral fluidic injectors incorporating diffusion stops.

FIG. 7 is a variant of the multi-injector device of FIG. 6 that includes a diffusion-stop. FIG. 7 shows a single micro-location of a planar device comprising at least one and possibly an array of micro-locations. FIG. 7A is a top view schematic and FIG. 7B is a side view schematic through the cross section ABB'A' of FIG. 7A. There is a micro-location 700 of a planar insulating substrate 701 with four spaced apart electrodes comprising two pumping pairs 702, 703 and 704, 705. There is an insulator 706 on the planar substrate covering the electrodes except at the openings 707, 708, 709 and 710 where contact is made to an overlaying hydrophilic matrix. The electrodes are connected elsewhere on the planar circuit to an external circuit providing power to the electrodes (not shown).

There are two formed hydrophilic matrix fluidic injectors, each comprising a reservoir and a transport path with one end connected to the reservoir and another effluent end. Each reservoir contains at least one chemical reagent to be pumped and the reagents in each reservoir can be different. The first injector has its reservoir 712 over opening 708 of electrode 703 and its transport path 711 fluidically connecting reservoir 712 to the micro-reactor 716 which is located at the effluent end B, with electrical contact through opening 707 to electrode 702 close to the effluent end. The second injector has its reservoir 714 over opening 710 of electrode 705 and its transport path 713 fluidically connecting reservoir 714 to the micro-reactor 716 which is located at the effluent end B', with electrical contact through opening 709 to electrode 704 close to the effluent end. The micro-reactor region also comprises a hydrophilic matrix 716. The effluent ends of the hydrophilic matrix transport paths 711 and 712 are separated from the hydrophilic matrix of the reactor by air gaps 720 and 721. A gas permeable insulator 715 overlays and fully encloses each of the fluidic injectors including the air gaps 720 and 721, but there is an opening in the enclosing insulator beyond the air gap over the hydrophilic matrix of the micro-reactor location 716.

In use of this device the planar micro-location is brought into contact with aqueous fluid (contained for example in a micro-channel 717 shown in FIG. 7B but, equally possible, contained in a micro-well or other conventional fluidic chamber of the art). Water vapor permeates through gas permeable insulator 715 and wets-up the enclosed hydrophilic matrix injectors. The aqueous fluid in the channel 717 or other aqueous fluids subsequently introduced into the channel can contain a sample to be reacted at micro-reactor 716 as well as other reagents. During this time the injectors are not fluidically connected to the reactor because of the air gaps 720 and 721. There is thus no opportunity for chemical reagents in the injector' reservoirs to move into the reactor until the injectors are powered by their respective electrodes. When a voltage is applied to 703 and 705 with respect to grounded 702 and 704 there is electro-osmotic propulsion of fluid within the injectors. The fluid being propelled out of the effluent end of the injectors displaces the air gap and then fluidically connects the injectors to the reactor, thus pumping integral reagent contained within the reservoir of the enclosed hydrophilic matrix into the reactor. Such a design is particularly valuable as the dimensions of the injector are scaled down. For an injector with a short transport path (for example a distance of less than 100 micrometers between the reservoir and the reactor) there can be significant diffusional leakage of reagent out of the reservoir into the reactor when there is no air gap to act as diffusion-stop.

Figure 8A:
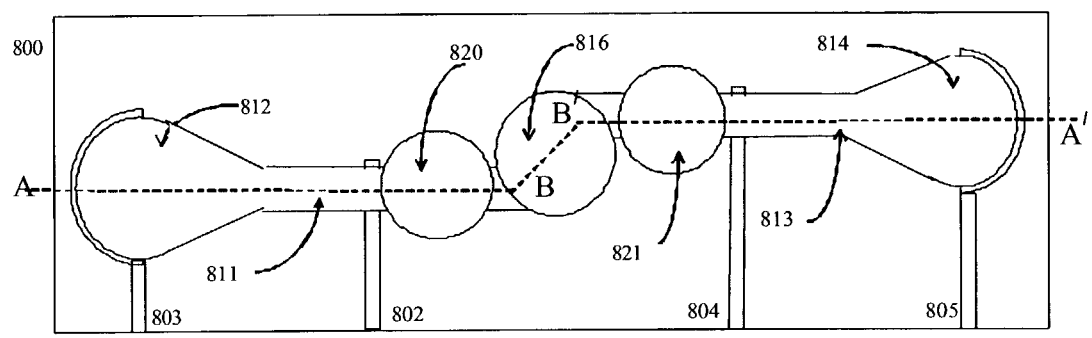
FIG. 8A is a schematic top plan view of a micro-location consisting of a micro-reactor and multiple integral fluidic injectors incorporating a separate pump reservoir and reagent reservoir.
Figure 8B:
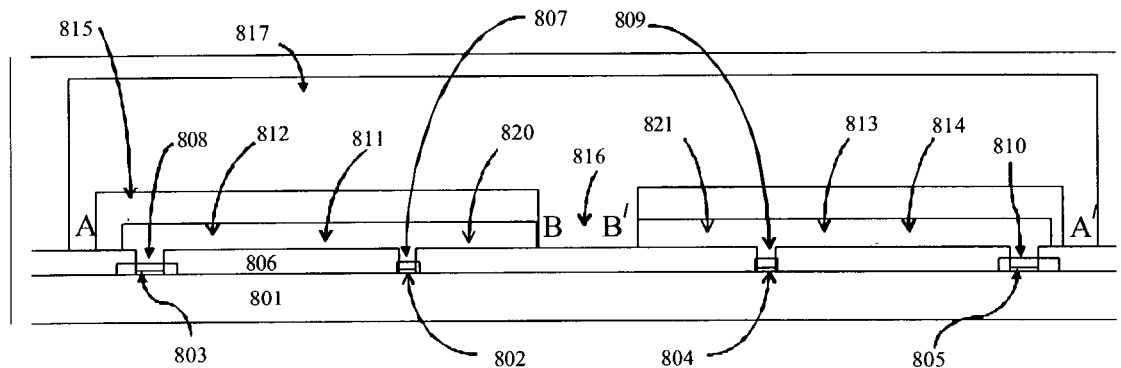
FIG. 8B is a schematic side view of a micro-location consisting of a micro-reactor and multiple integral fluidic injectors incorporating a separate pump reservoir and reagent reservoir.

FIG. 8 is another variant of the multi-injector device of FIG. 6 that includes a reagent reservoir downstream of a pump that pushes fluid and reagents out of the reservoir into an adjacent micro-reactor. FIG. 8 shows a single micro-location of a planar device comprising at least one and possibly an array of micro-locations. FIG. 8A is a top view schematic and FIG. 8B is a side view schematic through the cross section ABB'A' of FIG. 8A. There is a micro-location 800 of a planar insulating substrate 801 with four spaced apart electrodes comprising two pumping pairs 802, 803 and 804, 805. There is an insulator 806 on the planar substrate covering the electrodes except at the openings 807, 808, 809 and 810 where contact is made to an overlaying hydrophilic matrix. The electrodes are connected elsewhere on the planar circuit to an external circuit providing power to the electrodes (not shown).

There are two formed hydrophilic matrix fluidic injectors, each comprising a pump reservoir 812 and 814 and a transport path 811 and 813 with one end connected to the pump reservoir and another effluent end. At a location in each injector close to the effluent end of the transport path there is a reagent reservoir 820, 821. Each reagent reservoir contains at least one chemical reagent to be pumped and the reagents in each reservoir can be different. The first injector has its pump reservoir 812 over opening 808 of electrode 803 and its transport path 811 fluidically connecting pump reservoir 812 to the reagent reservoir 820 and then to the micro-reactor 816 located at the effluent end B, with electrical contact through opening 807 to electrode 802 close to the effluent end but upstream of the reagent reservoir 820. The second injector has its reservoir 814 over opening 810 of electrode 805 and its transport path 813 fluidically connecting pump reservoir 814 to the reagent reservoir 821 and then to the micro-reactor 816 located at the effluent end B', with electrical contact through opening 809 to electrode 804 close to the effluent end but upstream of the reagent reservoir 821. A gas permeable insulator 815 overlays and fully encloses each of the fluidic injectors except at their effluent end where there is an opening at the micro-reactor location 816.

In use of this device the planar micro-location is brought into contact with aqueous fluid (contained for example in a micro-channel 817 shown in FIG. 8B but, equally possible, contained in a micro-well or other conventional fluidic chamber of the art). Water vapor permeates through gas permeable insulator 815 and wets-up the enclosed hydrophilic matrix injectors. The aqueous fluid in the channel 817 or other aqueous fluids subsequently introduced into the channel can contain a sample to be reacted at micro-reactor 816 as well as other reagents. When a voltage is applied to 803 and 805 with respect to grounded 802 and 804 there is electro-osmotic propulsion of fluid within the injectors. The fluid being propelled out of the pump reservoir pushes reagent contained within the reagent reservoir out through the injector's effluent end into the micro-reactor. The material being expelled out of the injector's effluent end is that which is contained within the reagent reservoir. This design is particularly suitable to those instances where the contents of the injector's pump reservoir and the injector's transport path are not compatible with the reagents to be pumped into the reactor or the bioassay reaction taking place in the reactor. This incompatibility can manifest in one of two ways. Firstly if those materials required to operate the pump efficiently are deleterious to the bioassay reaction they should not be expelled from the effluent end of the injector. The pump reservoir and path may include for example humectants, redox materials and buffer salts that are necessary to optimize the injector's pumping characteristics and some or all of these materials may be deleterious to the bioassay reaction. Secondly, the reagent to be pumped may itself be deleterious to the efficient operation of the pump. For example the reagent may be high ionic strength or it may absorb on the walls of the hydrophilic matrix of the transport path thus diminishing the electro-osmotic coefficient of the pump or diminishing electrophoretic transport of the reagent. The reagent to be pumped may be electro-active and be electrochemically reacted at one of the pump's electrodes. Since the reagent reservoir is outside of the electric field region created between the injector's two pumping electrodes, the contents of the reagent reservoir necessary to be pumped into the reactor to perform the bioassay need not compromise the efficiency of the pump.

The devices shown schematically in FIGS. 1 to 3 and further described in the above in-use examples demonstrate how enclosed hydrophilic matrix circuits can be combined with a number of different conventional fluidic components, including chambers and conduits. To better appreciate the range of fluidic circuit arrangements that are possible using enclosed hydrophilic matrix devices and how such devices can be combined with conventional fluidic elements we describe below further detailed device configurations and their modes of use.

Figure 9A:
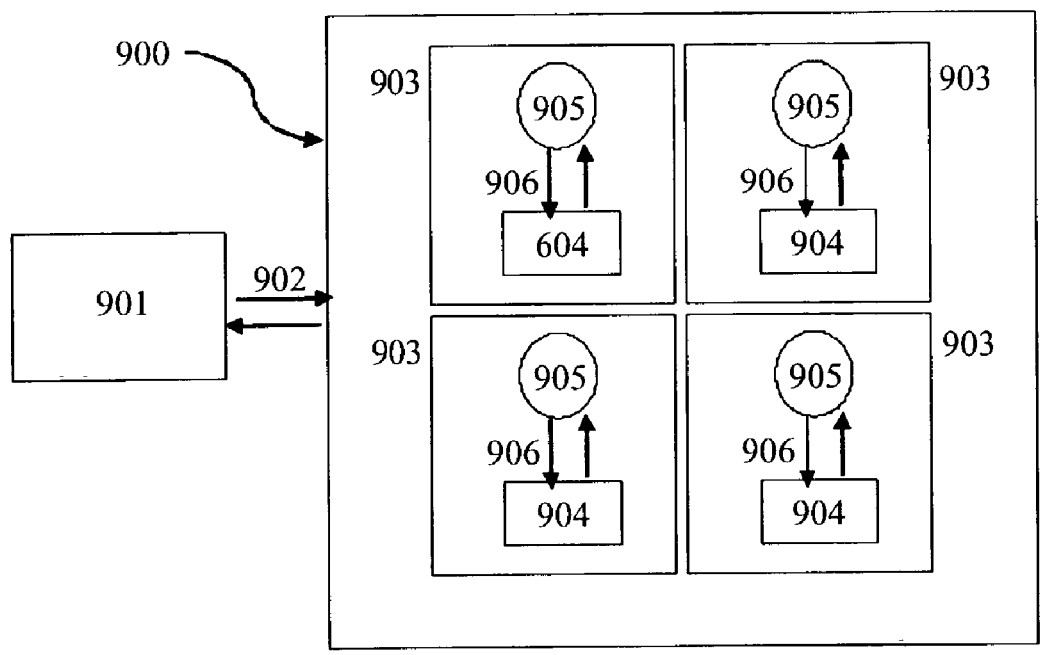
FIG. 9A is a schematic top plan view of an array of micro-locations consisting of a micro-reactors and integral nano-fluidic i/o and integral micro-fluidic i/o.

FIG. 9A describes one embodiment in a plan view schematic. The invented device is a single micro-location 903 or, as shown in the figure, an array 900 of micro-locations for performing chemical reactions. A micro-location of the array comprises of at least one micro-reaction site 905 and an integral nano-fluidic i/o device consisting of one or more pumps and reagent reservoir regions 904 connected to the micro-reactor(s) via transport paths 906. The nano-fluidic i/o device is an enclosed hydrophilic matrix circuit. As shown schematically by the arrows of 906, nano-liter volumes of fluids can be extracted from each micro-reactor or injected into it from the adjacent reservoirs; hence the term nano-fluidic i/o. FIG. 9A also shows a micro-fluidic i/o device consisting of one or more pumps and reagent reservoir regions 901 connected to the array 900 via transport paths 902. Larger micro-liter volumes of fluids can be extracted from each array or supplied to it from the adjacent reservoir; hence the term micro-fluidic i/o. The micro-fluidic i/o device is an enclosed hydrophilic matrix circuit. During use, at least some portions of the planar top surface of the device or array of FIG. 9 are contacted with at least one aqueous solution including the sample to be assayed.

Figure 9B:
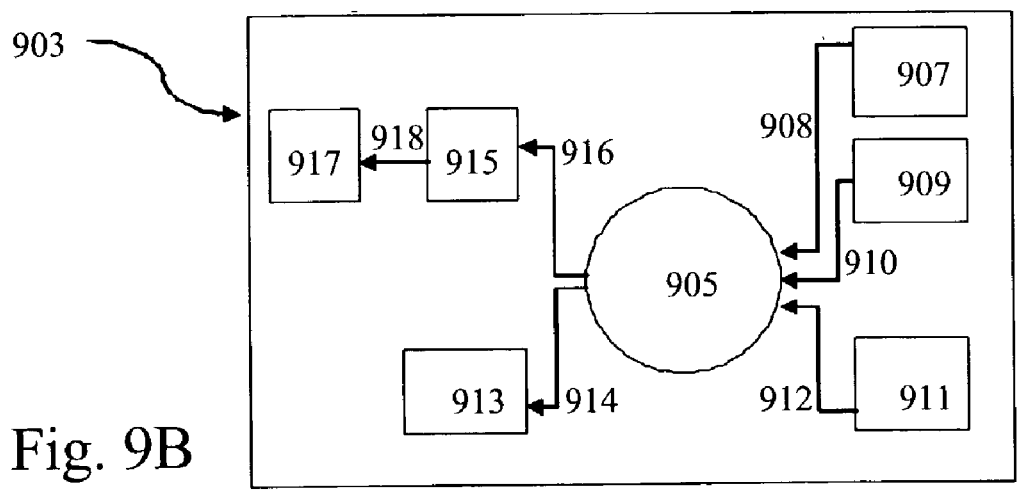
FIG. 9B is a schematic top plan view of a micro-location consisting of a micro-reactor and a detailed diagram of integral nano-fluidic i/o.

FIG. 9B shows an arrangement of the nano-fluidic i/o around a micro-reactor in more detail. There is shown an array of pumped reagent-containing reservoirs 907, 909 and 911 for fluid input to micro-reactor 905 along paths 908, 910 and 912 respectively. The inventor anticipates that the number of reservoirs and independently controlled pumps around a micro-reactor will be different in different bioassay devices, being determined by the format of the assay being performed. Also shown in FIG. 9B is a path 914 for extracting fluid from the micro-reactor to a reservoir 913 that functions as a waste chamber. In addition there is shown an optional path 916 for extracting fluid from the micro-reactor to a separation device 915 and then to waste 917 along path 918. Regions consisting of reagent reservoirs 907, 909, 911, separators 915, waste regions 913, 917 and paths 918 interconnecting regions and paths 908, 910, 912, 914, 916 connecting regions to the micro-reactor collectively constitute the nano-fluidic i/o comprising enclosed hydrophilic matrix devices. The number and type of nano-fluidic i/o elements and their arrangement is determined by the assay format.

Figure 10A:
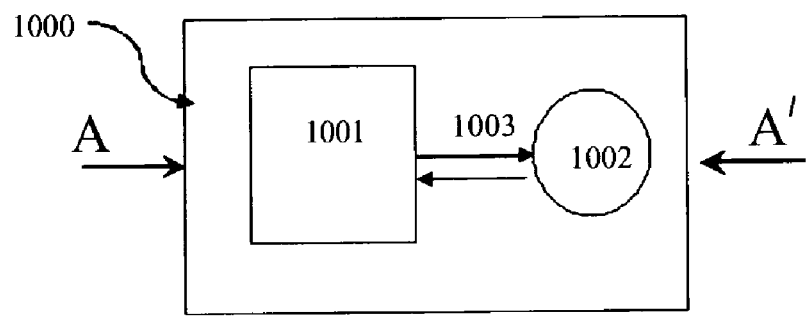
FIG. 10A is a schematic top plan view of a micro-location consisting of a micro-reactor in a well and integral nano-fluidic i/o.
Figure 10B:
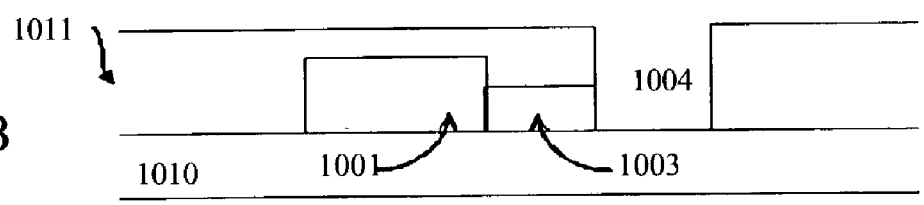
FIG. 10B is a schematic side view of a micro-location consisting of a micro-reactor in a well and integral nano-fluidic i/o comprising an enclosed hydrophilic matrix device.
Figure 10C:
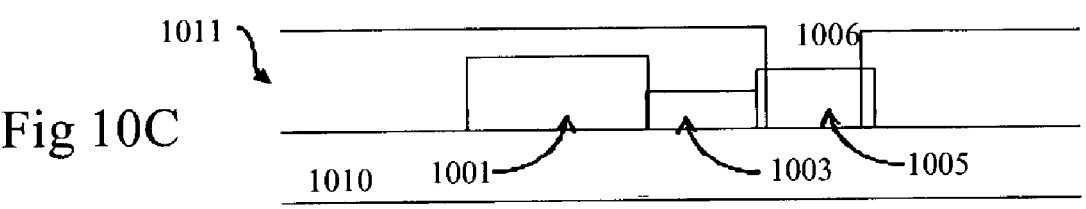
FIG. 10C is a schematic side view of a micro-location consisting of a micro-reactor in a well and integral nano-fluidic i/o comprising an enclosed hydrophilic matrix device.
Figure 10D:
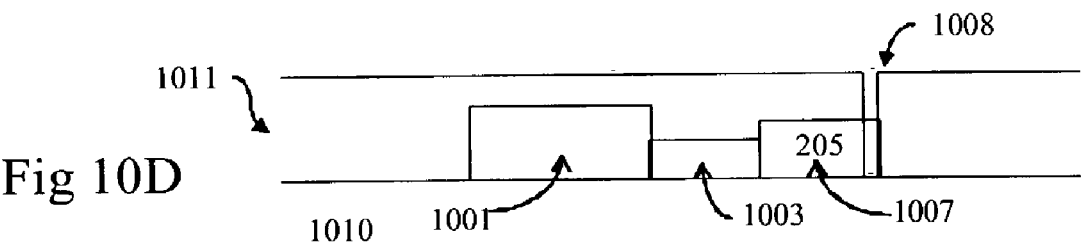
FIG. 10D is a schematic side view of a micro-location consisting of a micro-reactor in a well and integral nano-fluidic i/o comprising an enclosed hydrophilic matrix device.

FIG. 10A shows a plan view schematic of a micro-location 1000 comprising at least one micro-reactor 1002 and fluidic i/o comprising pumped reagent reservoirs 1001 and transport paths 1003. There is also shown in FIG. 10A a cross-section A–A'. FIGS. 10B–D show side-view schematics through the cross-section A–A' of FIG. 10A with various arrangements of micro-reactors and fluidic i/o according to this invention. FIG. 10B shows a schematic of a planar insulating substrate 1010 with reagent reservoir regions 1001 and paths 1003 connecting to a micro-reactor 1004. There is an insulator 1011 enclosing regions 1001 and paths 1003. Regions 1001 and paths 1003 consist of hydrophilic matrixes. Regions 1001 are reservoirs containing dry reagents. There is at least some portion of insulator 1011 capable of water vapor transport thus facilitating wet-up of the initially dry hydrophilic matrixes 1001 and 1003, during or prior to use. Wet-up occurs by transport of water from an aqueous solution immersing at least a part of the top surface of the device through at least a part of 1011 into the hydrophilic matrixes. The hydrophilic matrix regions 1001 and paths 1003 and the enclosing insulator 1011 together comprise an enclosed hydrophilic matrix circuit according to this invention. In the embodiment of FIG. 10B the micro-reactor 1004 is a micro-well defined on the planar surface by an opening in the insulator 1011.

FIG. 10C shows a schematic of an alternative arrangement of micro-reactor and fluidic i/o. The micro-reactor consists of a hydrophilic matrix 1005 in an opening 1006 in the insulator 1011. Reactions occur on or within 1005. Regions 1001 and paths 1003 and insulator 1011 comprise an enclosed hydrophilic matrix circuit that supplies the fluidic i/o's to the micro-reactor.

FIG. 10D shows still another alternative micro-reactor arrangement. The micro-reactor consists of a hydrophilic matrix 1007. The micro-reactor 1007 is connected by paths 1003 to regions 1001. Regions, paths and now also micro-reactors are enclosed within insulator 1011. An opening 1008 through insulator 1011 permits transport of fluid from an immersing electrolyte into the micro-reactor contained within the hydrophilic matrix circuit.

There are several ways known in the art for introducing sample and non-integral reagents to conventional planar micro-arrays. One widely used method is to take the planar micro-array, which is most commonly on a glass slide substrate and immerse the slide in a petri dish or similar open vessel. Sample is poured into the dish covering the entire top surface of the planar micro-array. A cover is placed over the petri dish. In another commonly used technique sample is introduced to the micro-array contained in a conventional micro-fluidic cartridge. The cartridge is a housing that forms a chamber for the sample with the planar micro-array forming one wall of the chamber. The chamber has an inlet orifice for sample introduction and an outlet orifice. The prior-art dishes and chambers described above are also appropriate to be used with the planar devices and arrays with integral fluidic i/o of this invention. FIGS. 11–12 describe other ways in which the devices of this invention can be interfaced with other sample chambers and fluidic elements.

Figure 11A:
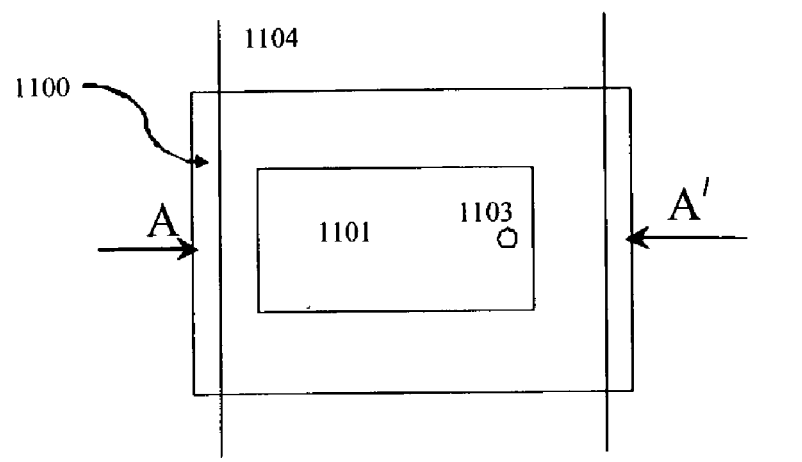
FIG. 11A is a schematic top plan view of a micro-location consisting of a micro-reactor in channel and integral nano-fluidic i/o.
Figure 11B:
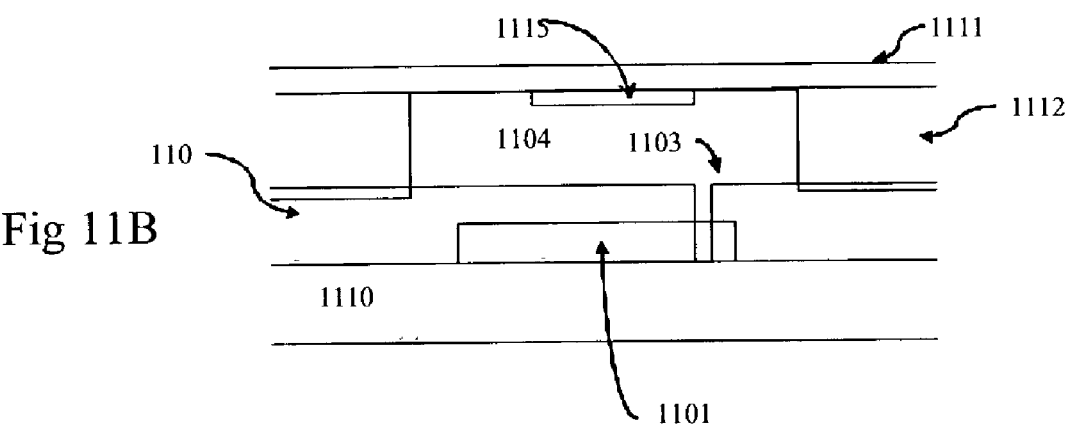
FIG. 11B is a schematic side view of a micro-location consisting of a micro-reactor in a channel and integral nano-fluidic i/o comprising an enclosed hydrophilic matrix device.
Figure 11C:
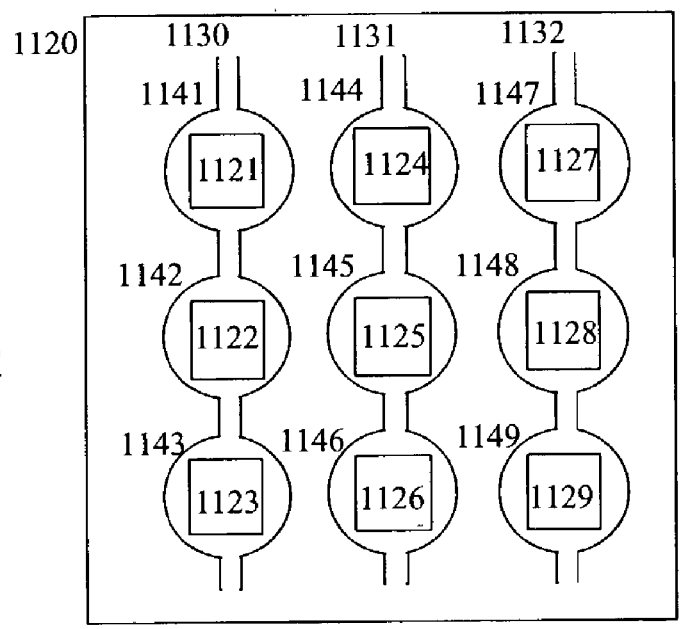
FIG. 11C is a schematic top plan view of an array of micro-locations consisting of micro-reactors in an array of channels and integral nano-fluidic i/o.

FIGS. 11A–11C are schematics of an embodiment in which the integrated fluidic i/o according to this invention is combined into a conventional fluidic channel.

FIG. 11A shows a plan view schematic of a micro-location 1100 comprising integral fluidic i/o 1101 which are enclosed hydrophilic matrix devices consisting of pumped reagent reservoirs and transport paths, fluidically connected to a channel 1104 through an orifice 1103. The fluidic i/o injects or extracts chemicals from the channel 1104.

FIG. 11B is a side view schematic through the cross-section A–A' of FIG. 11A. There is a planar insulating substrate 1110 with integral fluidics i/o component 1101 comprising one or more hydrophilic matrixes formed into reservoir regions, paths and optional micro-reactors. There is an insulator 1102 enclosing hydrophilic matrix components 1101. There is at least some portion of insulator 1102 capable of water vapor transport thus facilitating wet-up of the dry hydrophilic matrixes 1101, during or prior to use. The planar substrate 1110 and integral fluidic i/o provided by the enclosed hydrophilic matrix circuit is interfaced to other planar insulating element 1111 and 1112 with a channel 1104 such that the micro-location 1100 or an array of micro-locations are contained within the channel. Fluid can be introduced into and moved along conventional micro-fluidic channel 1104 by conventional fluidic pumping means including by capillary electro-kinetic pumping or pneumatic pumping. Wet-up occurs by transport of water from an aqueous solution introduced into channel 1104 that immerses at least a part of the top surface of the hydrophilic matrix circuit 1101 through at least a part of 1102 into the hydrophilic matrixes. An opening 1103 through insulator 1102 fluidically connects the enclosed hydrophilic matrix circuit 1101 with the fluid in the channel 1104, permitting transport of reagents out of the enclosed hydrophilic matrix circuit into the fluid in the channel 1104. In an alternative use of this device a fluid including a dissolved sample for assay contained in the channel 1104 can be introduced into a micro-reactor that is contained within the enclosed hydrophilic matrix circuit.

The channel cover elements 1111, 1112 with channels 1104 may be fabricated as a single component. Channels 1104 are formed using methods known in the art such as by laser ablation, etching or molding techniques. Alternatively, as shown in the figure, the cover elements may be two components 1111 and 1112 sealed in the final assembly. In this case 1111 is a planar slab and 1112 is a slab with slots or a formed gasket element fabricated on either planar substrate 1110 or planar slab 1111.

There is an optional reagent 1115 deposited on planar slab 1111. For example 1111 comprises capture molecules immobilized on its surface. In use of the device of FIG. 11 including capture reagent 1115, the planar slab is first reacted with a test sample so as to capture sample molecules on capture sites as is done in the conventional micro-array experiment. The slab 1111 is now assembled with the slab 1110 containing integral fluidic i/o devices, so that there is a fluidic i/o device and a capture site at each micro-location within the fluidic channels of the device. Reagents are introduced into the micro-reactor from the integral fluidic i/o device to complete the bioassay.

FIG. 11C shows how an array 1120 of micro-locations 1121–1129 comprising integral fluidic i/o according to this invention can be arranged in conventional micro-fluidic channels of the prior art 1130, 1131 and 1132. The channel 1130 connects an array of chambers 1141–1143, channel 1131 connects chambers 1144–1146 and channel 1132 connects chambers 1147–1149. Thus there is formed an array of chambers connected fluidically using prior-art fluidic channels each containing a micro-location with integral fluidic i/o of the current invention.

Figure 12A:
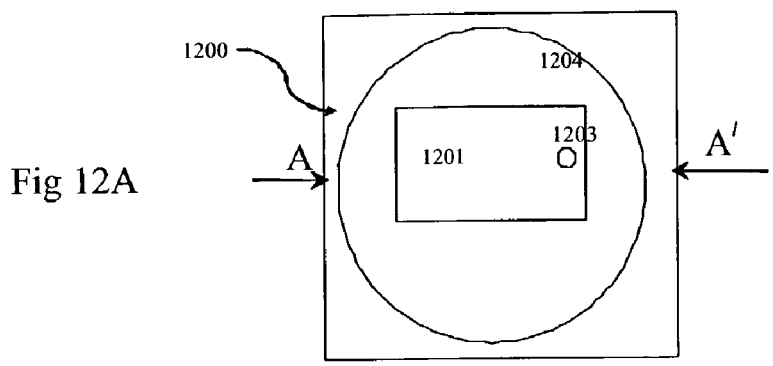
FIG. 12A is a schematic top plan view of a micro-location consisting of a micro-reactor in a well and integral fluidic i/o.
Figure 12B:
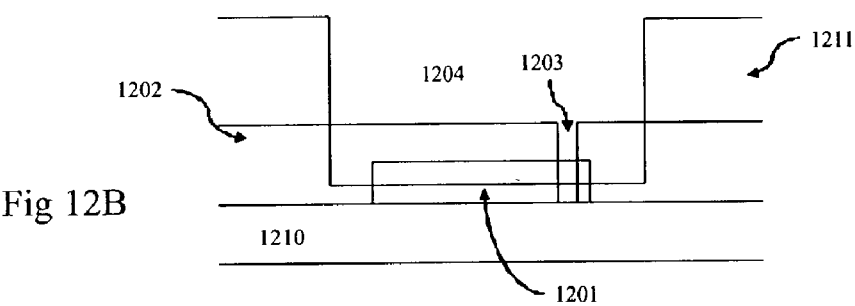
FIG. 12B is a schematic side view of a micro-location consisting of a micro-reactor in a well and integral fluidic i/o.

FIGS. 12A and 12B are schematics of an embodiment in which a micro-reactor and integrated fluidic i/o according to this invention is combined into a well or an array of wells of a conventional prior-art micro-plate.

FIG. 12A and 12B show a plan view and side view schematic respectively of a micro-location 1200 comprising integral fluidic i/o. There is a planar insulating substrate 1210 with integral fluidics i/o component 1201 comprising one or more hydrophilic matrixes formed into reservoir regions, paths and optional micro-reactors. There is an insulator 1202 enclosing hydrophilic matrix components 1201. There is at least some portion of insulator 1202 capable of water vapor transport thus facilitating wet-up of the dry hydrophilic matrixes 1201, during or prior to use. The planar substrate 1210 and integral fluidic i/o provided by the enclosed hydrophilic matrix circuit is interfaced to another planar insulating element 1211 with a well 1204 such that the micro-location 1200 is contained within the well. Fluid can be introduced into well 1204 by dispensing means connected to conventional fluidic pumping means including capillary electro-kinetic pumping or pneumatic pumping as are known in the art of micro-plate fluidics. Wet-up occurs by transport of water from an aqueous solution introduced into well 1204 that immerses at least a part of the top surface of the hydrophilic matrix circuit 1201 through at least a part of 1202 into the hydrophilic matrixes. An opening 1203 through insulator 1202 fluidically connects the enclosed hydrophilic matrix circuit 1201 with the fluid in the well 1204, permitting transport of reagents out of the enclosed hydrophilic matrix circuit into the fluid in the well 1204. An array of wells 1204 in slab 1211 comprises a micro-plate wherein each micro-well is fluidically connected to an integral fluidic i/o device of this invention.

FIGS. 12C–12F show a variant of the above device. This variant is a micro-well or a micro-well array with a cover plate.

Figure 12C:
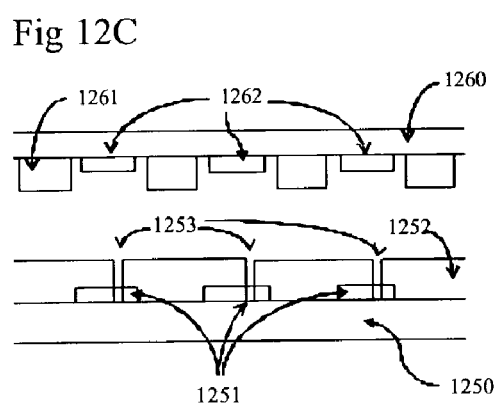
FIGS. 12C–12F are schematic side views of a micro-well array being assembled with integral fluidic i/o devices.
Figure 12D:
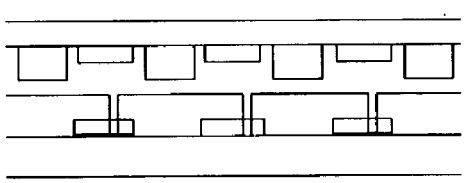
Figure 12F:
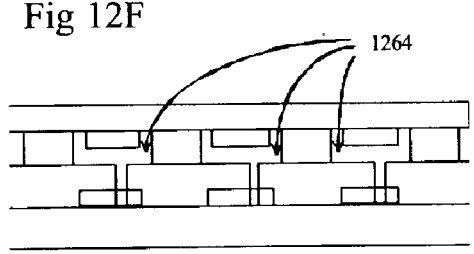
Figure 12E:
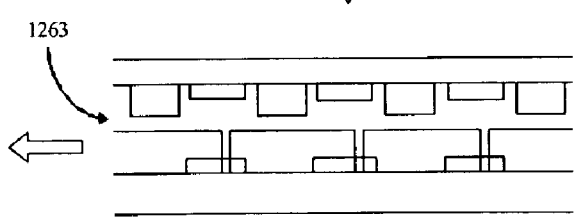

As shown in FIG. 12C there is a planar substrate 1250 with an array of micro-locations each micro-location comprising a fluidic i/o device comprising a hydrophilic matrix circuit 1251 enclosed by insulator 1252 with an orifice 1253. There is a cover plate is a planar slab 1260 which comprises an array of micro-locations with reagents 1262. The step and repeat dimensions of the array of micro-locations on slab 1260 is the same as the step-and-repeat dimensions of the array of integral fluidic i/o devices on the planar substrate 1250. In one use of this device the cover slab 1260 with its array may be first immersed into a test solution exposing the array of micro-locations to chemical reaction with the test solution. In this mode of use the cover slab and array of micro-locations is similar to a standard micro-array of the known art. For example 1260 might be a planar substrate comprising an array of capture sites such as in a protein array or a DNA array of the art. When exposed to a test fluid there are binding reactions in which components of the test solution bind at complimentary sites as is known in the art. The slab is then assembled in alignment and in close proximity but separated from the array of fluidic i/o devices as shown in FIG. 12D. Aqueous fluid 1263 is introduced between the two plates which are in proximity (FIG. 12E) and then the two plates are clamped together. When the plates are clamped, as shown in FIG. 12F the array of wells remains filled with fluid but each well is isolated from the others by the well wall element 1261. The bioassay procedure continues by pumping reagents into each of the isolated wells of the well-array from the integral fluidic i/o contained within each of the isolated wells. The bioassay reaction is monitored by standard techniques known in the micro-array or micro-plate art such as by optical means.

In another mode of use of this device the two plates are brought into proximity (FIG. 12D), test fluid is introduced between the plates (FIG. 12E) and then they are clamped together. In this example the reagent on a micro-location of slab 1260 only interacts with the fluid contained within the isolated well.

Figure 13:
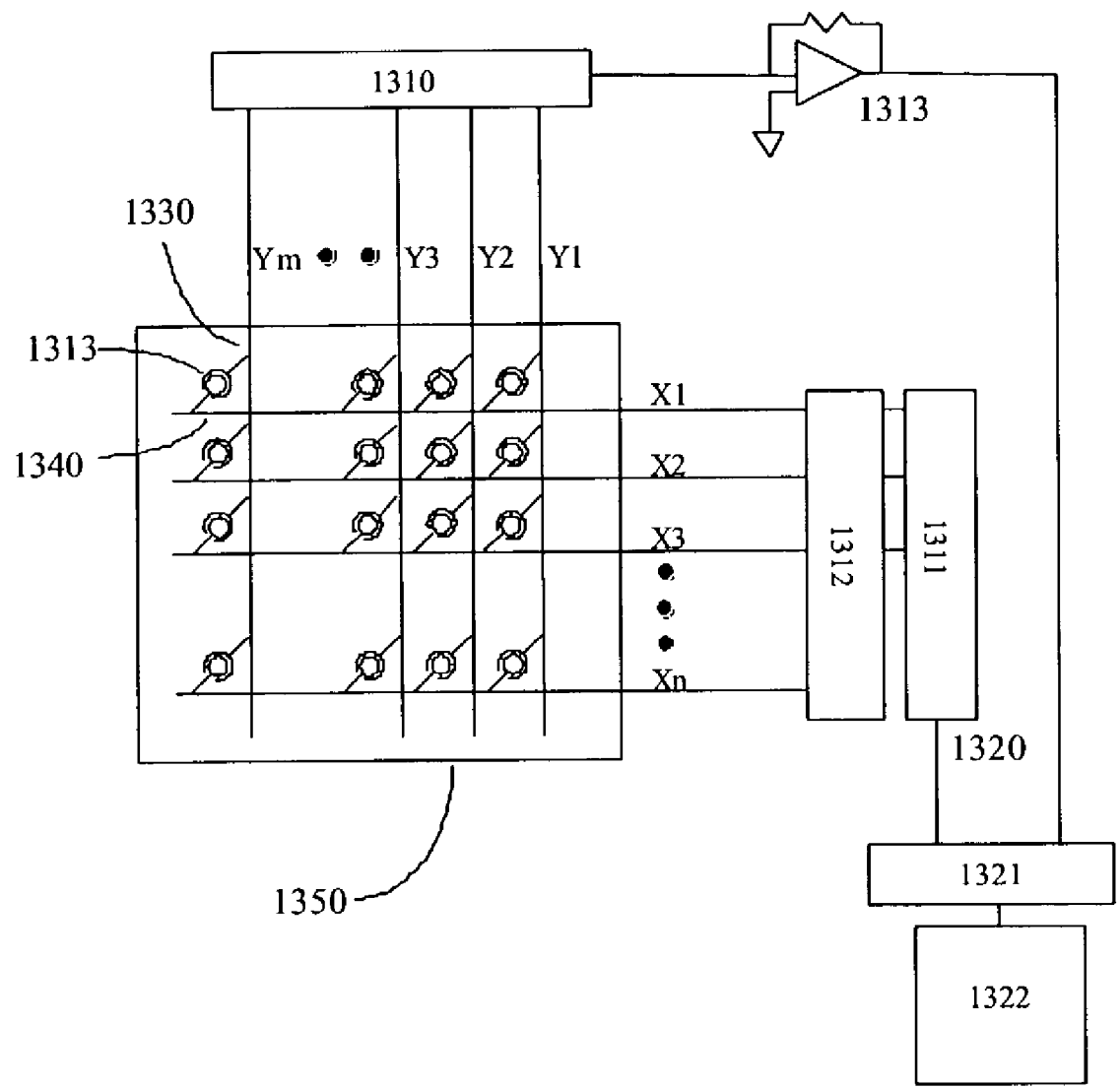
FIG. 13 is a block schematic circuit of an electro-kinetic pump array and its electrical connection.

FIG. 13 illustrates how an array of integral electro-kinetic injector pumps according to this invention can be electrically connected.

The most flexible electrical connection of a pump array allows independent addressing of each pumped location of the array. Preferably each pumped location is addressed site-specifically and independently of all others. In FIG. 13 there is shown an array of micro-locations on a planar substrate 1350. At each micro-location there is a micro-reactor and an integral fluidic i/o device comprising an enclosed hydrophilic matrix injector of this invention. Each injector 1313 has two electrodes for supply of electro-kinetic pump power. One electrode is connected to a horizontal row electrode 1340 the other to a vertical column electrode 1330. There is an array of row electrode contacts for connection to external circuits at one side of the planar device 1350 and an array of column electrode contacts on another side.

The scanning circuits for powering the pumps at each micro-location are similar to those used to power a matrix LCD display. For low cost applications we prefer a passive matrix control scheme similar to PMLCD matrix addressing technology known in the art.

There are two possible ways to drive the pump array: line-by-line and pixel-by-pixel (micro-location by micro-location). In the line-by-line address mode, columns Y1, Y2, Y3 . . . Ym are sequentially connected to ground from open circuit through the shift register and switch array 1310. With Y1 connected, voltages $V_{11}$ $V_{21}$ $V_{31}$. . . $V_{n1}$ are applied simultaneously through rows X1 X2 X3 . . . Xn. (writing line-by-line). Row voltages are obtained from a serial data stream from the computer's 1321 DAC applied to a shift register 1311 and sample and hold buffers 1312. Next when Y2 is connected, voltages $V_{12}$ $V_{22}$ $V_{32}$. . . $V_{n2}$ are applied through the row lines. And so on through the array. In the pixel-by pixel address mode, columns are addressed as above but now we apply row voltages sequentially by connecting each row in turn to the DAC from open circuit through a switch array. The column current is a serial string containing pixel-by-pixel data. This can be used for feedback control. The pixel-by-pixel address mode is much slower than row by row.

A biochip with 10,000 micro-locations will require 100 rows and 100 columns connection capability for a total of 200 contacts. Since the biochip is a unit-use disposable, the 200 connections are made to a high density contacting device designed for repeat contacting (such as those known in the art of electronic test or burn-in applications). Appropriate technologies are z-action connectors used for high density packaged IC testers, pogo-pin arrays as used in electronic component circuit testers or even z-action metal pin technology as used in direct contact to chip pads in chip testers are appropriate. QFP IC package test and burn-in sockets are preferred off-the-shelf items that can be used in this application. These devices enable contacts to devices with hundreds of pins per side enabling make and break repeat contact to high density arrays of this invention.

The two-electrode pump array of FIG. 13 can be fabricated using a two metal level planar process. The first metal level is deposited on a planar substrate and an array of horizontal, row-electrode elements is fabricated by photo-processing. An isolation insulating layer is next deposited on the row-electrodes with openings at each pump connection site. Next, a second level metal is deposited and an array of vertical, column-electrode elements is fabricated by photo-processing. A second isolating insulator is deposited on the column electrodes with openings at each pump connection site. In this way there is a pair of electrodes at each pump location. The cross-over points of the array of rows and columns are electrically isolated. The device is completed by fabricating an enclosed hydrophilic matrix device over each pair of electrodes of the square array to result in an enclosed hydrophilic matrix injector at each micro-location.

In use the planar device is immersed in one or more test solution as required to perform a multiplicity of bio-assay reactions, one at each micro-location of the array. Fluids incorporating reagents are brought to each micro-reactor of the array by electro-kinetic pumping from integral reservoirs, as described below. The course of a reaction in a micro-reactor of the array is monitored by a detection means, and the course of an array of reactions on the planar device is monitored by a detector array. Such detector arrays are known in the art and include optical scanners and CCD cameras when using the preferred optical detection means.

Feedback control of the pump power is a preferred mode of use. There are two ways to implement feedback control. The best way is to incorporate an optical label into the pump reservoir. This chemical will be pumped alongside the bioassay reagents, but it does not participate in the reaction. The concentration of the label can be measured by the same read-out system used for the bioassay. In another scheme, we can measure the pump current at each site and use this signal for feedback control. In the line-by-line address mode we can operate feedback control by controlling on site-specific optical data but not on the pump current, because we do not measure it at each site.

Although specific embodiments of the invention have been described herein for purposes of illustration, various modifications may be made without deviating from the spirit and scope thereof.

What is claimed is:

1. An enclosed hydrophilic matrix device for transport of an aqueous solute, comprising
an electrically insulated substrate;
a hydrophilic matrix path on the substrate for electrokinetic transport of the solute, the matrix path having a pair of spaced apart contacting locations for respective electric contact with a source of power for producing an electric potential along the hydrophilic matrix path;
an electrode supported on the substrate and having a contact end for connection to the power source and a matrix end for electric contact with the hydrophilic matrix at one of the contacting locations;
the hydrophilic matrix being initially dry and including a humectant for increasing a water absorption rate of the matrix;
an insulator enclosing the hydrophilic matrix for sealing the matrix between the insulator and the substrate, the insulator being made of a water vapor permeable material impermeable to the solute; and
an orifice in the insulator above the matrix for the passage of an aqueous solute through the insulator.

2. The device of claim 1, including a pair of electrodes supported on the substrate, each electrode having a contact end for connection to the power source and a matrix end for electric connection to the hydrophilic matrix at one of the contacting locations.

3. The device of claim 2, wherein electric contact between the matrix and the electrodes at the contact locations is achieved by direct physical contact between the electrode and matrix materials at the contacting locations.

4. The device of claim 2, wherein the electrodes and matrix path are spaced apart at the contact locations and electric contact is achieved by an intermediate conductive substance.

5. The device of claim 2, wherein the electrodes and matrix path are spaced apart at the contact locations and electric contact therebetween is achieved by a hydrophilic intermediate substance which has an initially dry and non conductive condition and a humidified and conductive condition and is in contact with the matrix for passage of water from the matrix, when in the humidified condition, into the intermediate substance.

6. The device of claim 2, wherein the electrodes and matrix path are spaced apart at the contact locations and electric contact therebetween is achieved by a hydrophilic substance included in the matrix at the contacting locations, which substance has an initially dry and non conductive condition and a humidified and conductive condition and is in contact with the matrix for passage of water from the matrix, when in the humidified condition, into the substance, the substance electrically connecting the electrodes with the matrix at the contacting locations in the humidified condition.

7. The device of claim 2, wherein one of the pair of electrodes is constructed as a cathode electrode for supporting an oxygen reduction reaction, and the enclosing insulator is gas permeable for permitting lateral diffusion of oxygen through the insulator.

8. The device of claim 2, wherein one of the pair of electrodes is constructed as an anode electrode for supporting a water oxidation reaction, and the enclosing insulator is gas permeable for permitting oxygen removal from the electrode region by lateral permeation through the gas permeable insulator.

9. The device of claim 8, wherein the hydrophilic matrix further contains dry-etchable additives.

10. The device of claim 9, wherein the hydrophilic matrix reservoir region is circular and contains reagents locally deposited from a micro-nozzle dispenser, ink jet dispenser or a pin-transfer dispenser.

11. The device of claim 9, wherein the hydrophilic matrix path for solute transport includes an air gap located between the matrix reservoir and the orifice in the insulator.

12. The device of claim 9, the matrix further including a second hydrophilic matrix reservoir interposed between the other electrode and the orifice.

13. The device of claim 12, wherein the second reservoir contains a reagent to be electro-kinetically pumped through the orifice.

14. A planar array of hydrophilic matrix fluidic i/o devices, comprising an array of micro-locations each including a hydrophilic matrix fluidic i/o device as defined in claim 9.

15. The device of claim 2, wherein the substrate has a pair of opposite surfaces, the matrix path is supported on one of the substrate surfaces and at least one of the pair of electrodes is supported on the other substrate surface, the substrate being shaped and constructed for providing electrical contact of the matrix with the electrode on the opposite substrate surface.

16. The device of claim 15, wherein the substrate includes a passage for physical and electrical contact of the matrix at one of the contacting locations with the electrode on the opposite substrate surface.

17. The device of claim 15, wherein the pair of electrodes are supported on one of the substrate surfaces and the matrix is supported on the opposite of the substrate surfaces and the substrate at each of the contacting locations has a throughgoing passage, the matrix material extending through the passage and into contact with the respective electrode.

18. The device of claim 1, wherein the hydrophilic matrix has a dry and inactive state in which it is substantially non-conductive, and a humidified and active state, the hydrophilic matrix being transferable from the inactive state into the humidified state by incorporation of water vapor.

19. The device of claim 18, wherein the insulator is gas permeable to permit incorporation of water into the matrix by capillary action through the orifice.

20. The device of claim 18, wherein the insulator includes a wet-up opening for the passage of water and is gas permeable to permit venting of gas within the enclosed matrix during incorporation of water into the matrix by capillary action through the wet-up opening.

21. The device of claim 1, wherein the humectant is a low molecular weight neutral molecule which when dissolved in water forms an aqueous solution with a water vapor pressure significantly less than pure water at a concentration where the solution's viscosity is not significantly higher than pure water.

22. The device of claim 21, wherein the humectant is selected from the group of urea, alanine, orthinine, praline, lysine, glycine, polyols and sugars: sucrose, glucose, xylitol, sorbitol, mannitol, lactose, maltose, lactulose, glycerol, propylene glycol, citric acid, tartaric acid, malic acid and combinations thereof.

23. The device of claim 1, wherein the hydrophilic matrix path has a fixed charge for electro-osmotic transport of the aqueous solute therethrough.

24. The device of claim 23, wherein the reagent is in a dry state when the matrix is in the dry state, the reagent in the dry state being substantially positionally and chemically stable.

25. The device of claim 1, wherein the hydrophilic matrix contains a reagent to be electro-kinetically pumped through the orifice.

26. The device of claim 1, wherein the hydrophilic matrix contains electrolyte salt.

27. The device of claim 26, wherein the maximum electrolyte salt concentration in the matrix is 10 mM.

28. The device of claim 27, wherein the neutral humectant is loaded to give a wet-up concentration of greater than 1 molar in the humidified state of the matrix.

29. The device of claim 28, wherein the redox additive is neutral.

30. The device of claim 29, wherein micro-pores of the matrix have a diameter between 50 nanometers and 5 micrometers.

31. The device of claim 1, wherein the humectant is a neutral molecule.

32. The device of claim 1, wherein the hydrophilic matrix further contains a redox additive.

33. The device of claim 1, wherein the hydrophilic matrix is micro-porous.

34. The device of claim 1, wherein the hydrophilic matrix has a maximum thickness of 50 micrometers.

35. The device of claim 1, wherein the water vapor permeable insulator is less than 25 micrometers in thickness.

36. The device of claim 1, wherein the hydrophilic matrix material is selected to be dry-etchable.

37. The device of claim 1, wherein the hydrophilic matrix path further includes a reservoir for containing a reagent to be transported along the matrix path by electrokinetic transport.

38. A micro reactor device with integrated fluidic i/o, comprising
 an insulated substrate;
 a pair of electrodes supported on the substrate, each electrode having a contact end for connection to an external circuit for supplying power and a matrix end for electric contact with a hydrophilic matrix;
 a hydrophilic matrix path on the substrate for electro-kinetic transport of the solute, the matrix path including a reservoir for containing a reagent, a transport path for electro-kinetic transport of the reagent, a discrete micro-reactor for carrying out a chemical reaction and a pair of spaced apart contacting locations for electric contact with the respective matrix ends of the electrodes, the matrix being initially dry and including a humectant for increasing a water absorption rate of the matrix;
 an insulator enclosing the hydrophilic matrix for sealing the matrix between the insulator and the substrate, the insulator being made of a vapor permeable material impermeable to the solute; and
 an orifice in the insulator above the matrix for the passage of an aqueous solute through the insulator.

39. A planar micro-reactor array, comprising an array of micro-locations, each including a micro-reactor device as defined in claim 38.

40. The array of claim 39, wherein each reactor device is constructed to carry out a nucleic acid hybridization reaction.

41. The array of claim 39, wherein each reactor device is constructed to carry out a protein-protein interaction.

42. A micro reactor device as defined in claim 38, including a plurality of reservoirs each containing a different reagent for transport to the micro-reactor.

43. A micro reactor device as defined in claim 38, including a plurality of micro-reactors for receiving the reagent from the reservoir.

44. A micro reactor device as defined in claim 38, wherein the orifice is located between the reservoir and the micro-reactor.

45. A micro reactor device as defined in claim 44, wherein the matrix path includes a first portion extending between the contacting locations and a second portion in extension of the first portion, the device further comprising a gap in the matrix path for preventing osmotic transport thereacross of the reagent in the reservoir, the gap being located in the first portion and between the reservoir and the micro reactor.

46. A micro reactor device as defined in claim 38, wherein the matrix path includes a first portion extending between the contacting locations and a second portion in extension of the first portion, the reservoir being positioned in the second portion and the orifice being located in the second portion between the reservoir and the first portion.

47. A micro reactor device as defined in claim 38, wherein the matrix path includes in series a first portion, a second portion and a third portion, the second portion extending between the contacting locations, the reservoir being located in the first portion and the orifice and the micro-reactor being located in the third portion.

48. A micro reactor device as defined in claim 47, further comprising a second reservoir located in the second portion.

49. A micro reactor device as defined in claim 48, further comprising a gap in the matrix path in one of the second and third portions for preventing osmotic transport of the solute thereacross, the gap being located between the second reservoir and the orifice.

50. A micro reactor device as defined in claim 49, wherein the gap is located in the second portion between the reservoir and the third portion.

51. A bioassay device, comprising a first and a second micro reactor device as defined in claim 35 and, the second micro reactor device being arranged in series to the first micro reactor device such that the matrix path of the second micro reactor device is separated from the matrix path of the first micro reactor device by an intermediate air gap which can be bridged through electrokinetic pumping along the matrix path of the first micro reactor device.

52. A bioassay device, comprising in combination an enclosed hydrophilic matrix fluidic i/o device according to claim 9 and a micro reactor device with integrated fluidic i/o, comprising
 an insulated substrate;
 a pair of electrodes supported on the substrate, each electrode having a contact end for connection to an external circuit for supplying power and a matrix end for electric contact with a hydrophilic matrix;
 a hydrophilic matrix path on the substrate for electro-kinetic transport of the solute, the matrix path including a reservoir for containing a reagent, a transport path for electro-kinetic transport of the reagent, a discrete micro-reactor for carrying out a chemical reaction and a pair of spaced apart contacting locations for electric contact with the respective matrix ends of the electrodes, the matrix being initially dry and including a humectant for increasing a water absorption rate of the matrix;
 an insulator enclosing the hydrophilic matrix for sealing the matrix between the insulator and the substrate, the insulator being made of a water vapor permeable material impermeable to the solute; and an orifice in the insulator above the matrix for the passage of an aqueous solute through the insulator;

the orifice in the insulator of the hydrophilic matrix fluidic i/o device overlapping the orifice in the insulator of the reactor device for reagent exchange and the hydrophilic matrix fluidic i/o device being constructed for electro-kinetically transporting the reagent from the reservoir to the reactor device through the orifice.

53. A bioassay device, comprising a first planar array in accordance with claim 52 and having the micro-reactor devices arranged at preselected step-and-repeat dimensions;

a second planar array of micro-locations each including an immobilized reactant and being arranged at the same step-and-repeat dimensions as the micro-reactor devices in the first array;

alignment means for aligning the co-planar first and second arrays in a spaced apart parallel orientation so that the micro-reactors on the respective arrays are aligned pairwise opposite to one another;

means for introducing fluid between the co-planar first and second arrays; and means for sealing each pair of micro-reactor and opposite micro-location for forming an array of isolated, fluid-filled wells, each well containing a micro-reactor of the first array, a spaced apart parallel micro-location of the second array and intermediate fluid.

54. A bioassay device, comprising a first planar micro-reactor array having an array of micro-locations, each including a micro-reactor device and having the micro-reactor devices arranged at preselected step-and-repeat dimensions;

each micro reactor device including an insulated substrate;

a pair of electrodes supported on the substrate, each electrode having a contact end for connection to an external circuit for supplying power and a matrix end for electric contact with a hydrophilic matrix;

a hydrophilic matrix path on the substrate for electro-kinetic transport of the solute, the matrix path including a reservoir for containing a reagent, a transport path for electro-kinetic transport of the reagent, a discrete micro-reactor for carrying out a chemical reaction and a pair of spaced apart contacting locations for electric contact with the respective matrix ends of the electrodes, the matrix being initially dry and including a humectant for increasing a water absorption rate of the matrix;

an insulator enclosing the hydrophilic matrix for sealing the matrix between the insulator and the substrate, the insulator being made of a water vapor permeable material impermeable to the solute; and an orifice in the insulator above the matrix for the passage of an aqueous solute through the insulator;

a second planar array in accordance with claim 29 and having the hydrophilic matrix fluidic i/o devices arranged at the same step-and-repeat dimensions as the micro-reactors in the first array;

alignment means for aligning the co-planar first and second arrays in a spaced apart parallel orientation so that each micro-reactor on the first planar array is opposite one hydrophilic matrix fluidic i/o device of the second array;

means for introducing fluid between the co-planar first and second arrays; and means for sealing each pairing of micro-reactor and opposite hydrophilic matrix fluidic i/o device for forming an array of isolated, fluid-filled wells, each well containing a micro-reactor of the first array, a spaced apart parallel hydrophilic matrix fluidic i/o device of the second array and intermediate fluid.

55. The bioassay device of claim 54, further comprising means for monitoring a reaction in each of the isolated wells.

* * * * *